(12) United States Patent
Saiki et al.

(10) Patent No.: US 8,865,472 B2
(45) Date of Patent: Oct. 21, 2014

(54) ANALYZING APPARATUS AND METHOD THAT USE CENTRIFUGAL FORCE

(75) Inventors: Hiroshi Saiki, Ehime (JP); Kouzou Tagashira, Ehime (JP); Kenji Watanabe, Ehime (JP); Kenji Ishibashi, Ehime (JP); Takuji Miyata, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 257 days.

(21) Appl. No.: 12/866,399

(22) PCT Filed: Feb. 4, 2009

(86) PCT No.: PCT/JP2009/000420
§ 371 (c)(1),
(2), (4) Date: Aug. 5, 2010

(87) PCT Pub. No.: WO2009/098866
PCT Pub. Date: Aug. 13, 2009

(65) Prior Publication Data
US 2010/0323454 A1  Dec. 23, 2010

(30) Foreign Application Priority Data

Feb. 5, 2008 (JP) ................. 2008-024624
Feb. 5, 2008 (JP) ................. 2008-024625
Apr. 24, 2008 (JP) ................. 2008-113265
Jan. 23, 2009 (JP) ................. 2009-012434

(51) Int. Cl.
| | |
|---|---|
| *G01N 21/07* | (2006.01) |
| *G01N 21/75* | (2006.01) |
| *G01N 1/38* | (2006.01) |
| *B01L 3/00* | (2006.01) |
| *G01N 35/04* | (2006.01) |

(52) U.S. Cl.
CPC ......... *G01N 21/07* (2013.01); *B01L 2400/0409* (2013.01); *B01L 3/50273* (2013.01); *B01L 2300/087* (2013.01); *B01L 2400/0406* (2013.01); *B01L 2300/0803* (2013.01); *G01N 2035/0449* (2013.01)
USPC ........... 436/164; 422/72; 422/82.05; 436/174

(58) Field of Classification Search
None
See application file for complete search history.

(56) References Cited

U.S. PATENT DOCUMENTS

| | | | |
|---|---|---|---|
| 5,591,643 | A | 1/1997 | Schembri |
| 8,158,079 | B2 | 4/2012 | Sugimoto et al. |

(Continued)

FOREIGN PATENT DOCUMENTS

| | | |
|---|---|---|
| CN | 1705884 | 12/2005 |
| JP | 4-504758 | 8/1992 |

(Continued)

OTHER PUBLICATIONS

International Search Report of PCT/JP2009/000420, dated Apr. 28, 2009.

*Primary Examiner* — Yelena G Gakh
*Assistant Examiner* — Michelle Adams
(74) *Attorney, Agent, or Firm* — Hamre, Schumann, Mueller & Larson, P.C.

(57) ABSTRACT

An analyzing device mixes a sample liquid with a reagent by rotation of the analyzing device about a rotation center to generate a centrifugal force. A measurement cell is formed so as to extend in a direction along which the centrifugal force is applied, and a capillary area to which the sample liquid is sucked by a capillary force is formed on one of the side walls of the measurement cell, the side walls being arranged in a rotational direction. The capillary area extends from the outer periphery position to the inner periphery of the measurement cell, thereby reducing the size of the analyzing device. Further, the sample liquid in the measurement cell is sucked to the capillary area by slowing or stopping a rotation, and then the rotation is accelerated to return the sample liquid in the capillary area to the measurement cell.

13 Claims, 40 Drawing Sheets

(56) References Cited

U.S. PATENT DOCUMENTS

2006/0008381 A1 1/2006 Taguchi et al.
2009/0205447 A1* 8/2009 Sugimoto et al. .......... 73/864.21

FOREIGN PATENT DOCUMENTS

| | | |
|---|---|---|
| JP | 5-508709 | 12/1993 |
| JP | 9-504732 | 5/1997 |
| JP | 2004-150804 | 5/2004 |
| JP | 2006-145451 | 6/2006 |
| JP | 2006-214955 | 8/2006 |
| JP | 2007-33225 | 2/2007 |
| JP | 2007-078676 | 3/2007 |
| JP | 2007-263707 | 10/2007 |
| WO | WO 90/13016 | 11/1990 |
| WO | WO 91/18656 | 12/1991 |
| WO | WO-2008/001796 A1 * | 1/2008 |

* cited by examiner

E-E SECTIONAL VIEW

F-F SECTIONAL VIEW

G-G SECTIONAL VIEW

H-H SECTIONAL VIEW

H-H SECTIONAL VIEW

I-I SECTIONAL VIEW

I-I SECTIONAL VIEW

J-J SECTIONAL VIEW

J-J SECTIONAL VIEW

F-F SECTIONAL VIEW

G-G SECTIONAL VIEW

K-K SECTIONAL VIEW

F-F SECTIONAL VIEW

G-G SECTIONAL VIEW

H-H SECTIONAL VIEW

K-K SECTIONAL VIEW

L-L SECTIONAL VIEW

ANALYZING APPARATUS AND METHOD THAT USE CENTRIFUGAL FORCE

TECHNICAL FIELD

The present invention relates to an analyzing device used for analyzing a liquid collected from an organism and the like, and an analyzing apparatus and an analyzing method using the analyzing device, and specifically relates to a technique of agitating a sample liquid and a reagent in a measurement cell of the analyzing device.

BACKGROUND ART

In the prior art, a liquid collected from an organism and the like is analyzed by a known analyzing method using an analyzing device having fluid channels formed therein. The analyzing device can control a fluid with a rotator. By using a centrifugal force, the analyzing device can dilute a sample liquid, measure a solution, separate a solid component, transfer and distribute a separated fluid, and mix a solution and a reagent, thereby enabling various biochemical analyses.

Patent document 1 describes an analyzing device for transferring a solution by a centrifugal force. As shown in FIGS. 38A and 38B, a sample liquid is injected into an inlet passage 114 from an inlet 116 by an inserting instrument such as a pipette, the sample liquid is transferred to a measurement cell 115 by a rotation of the analyzing device, the sample liquid is sucked by a capillary force, which is applied to a passage 117, by slowing or stopping the rotation, and then the sample liquid is returned to the measurement cell 115 by accelerating the rotation again, so that the sample liquid and a reagent are agitated.

For example, in an analyzing method of a sample liquid, a reaction liquid obtained by a reaction of the sample liquid and a reagent is analyzed by an optical technique in which multiple passages are provided to analyze multiple items of a single sample liquid or a single item of multiple sample liquids. FIG. 39 specifically shows an analyzing device of patent document 2.

In this configuration, a sample liquid 123 applied into a liquid receiving portion 118 is transferred to reaction chambers 119B of an analysis container through passages 119 of the analysis container by a centrifugal force and capillarity, the sample liquid 123 is reacted in the reaction chambers 119B with reagents 122 set in the reaction chambers 119B, and mixed solutions in the reaction chambers 119B are optically accessed to read the color reactions of the mixed solutions.

The analyzing device is made up of a base 120 (see FIG. 40A) on which the passages 119 and the reaction chambers 119B are formed of various recessed portions, and a cover 121 that is bonded to the top surface of the base 120 with an adhesive layer. Before the cover 121 is bonded to the top surface of the base 120, only a required quantity of liquid reagent is dropped into the reaction chamber 119B and is air-dried or freeze-dried. After that, the base 120 and the cover 121 are bonded to each other with the adhesive layer, so that the reagent 122 is set in the reaction chamber 119B.

Patent document 3 describes an analyzing method in which a sample is quantified, is reacted with a reagent, and then is detected by using a centrifugal force and a capillary force. FIG. 41 shows the technique of patent document 3.

In this analyzing device, in the direction of an arrow 315 from the side closest to an axis acting as a centrifugal force source to the outer periphery, there are provided a whole blood separating chamber 331 in which while blood (blood) 345 is injected as a specimen from an inlet 331a, a separating chamber 332, a quantifying chamber 333, and a reaction/detection chamber 334.

The whole blood separating chamber 331 and the separating chamber 332 are connected to each other via a passage 335, a reagent chamber 336, a passage 337, an agitating part 338, and a passage 339. The separating chamber 332 and the quantifying chamber 333 are connected to each other via a passage 340. The quantifying chamber 333 and the reaction/detection chamber 334 are connected to each other via a passage 341.

In the analyzing method of the prior art, the sample liquid prepared in the whole blood separating chamber 331 and the separating chamber 332 is transferred to the quantifying chamber 333 by applying a centrifugal force to the analyzing device. Further, an excessive quantity of the supplied sample liquid in the quantifying chamber 333 is discharged from an outlet 333c, so that the supplied sample liquid can be quantified according to the capacity of the quantifying chamber 333.

When the centrifugal force is stopped, the sample liquid fills the passage 341 up to an outlet 341c by a capillary force and is stopped by a surface tension. After that, a centrifugal force is applied again to the analyzing device, so that the whole sample liquid in the quantifying chamber 333 is transferred to the reaction/detection chamber 334. The sample liquid transferred to the reaction/detection chamber 334 reacts in contact with a reactant 343 and the absorbance of the reacted sample liquid is detected by an optical method, so that the sample liquid is analyzed.

Patent document 1: Japanese Patent Laid-Open No. 2006-145451
Patent document 2: Japanese Patent Laid-Open No. 2004-150804
Patent document 3: Japanese Patent Laid-Open No. 2006-214955

DISCLOSURE OF THE INVENTION

Problems to be Solved by the Invention

In patent document 1, however, the measurement cell 115 is orthogonal to a centrifugal direction and thus in an optical measurement on the sample liquid in the measurement cell 115, the measurement cell 115 has to be filled with a large quantity of the sample liquid. Thus it is difficult to reduce the quantity of the sample liquid.

Further, an agitating mechanism for agitating the sample liquid and the reagent is U-shaped and is made up of the inlet passage 114, the measurement cell 115, and the passage 117. This configuration has a waste space formed between the inlet passage 114 and the passage 117 and thus is not suitable for reducing the size of the analyzing device.

In patent document 2, the reagent 122 is set in the recessed portion of the reaction chamber 119B. The reagent 122 dropped into the reaction chamber 119B as shown in FIG. 40A may be set, as shown in FIG. 40B, on a wall surface of the recessed portion of the reaction chamber 1193 immediately after the dropping or during a dry process. Thus the reagent may be dried with a high concentration on the wall surface of the recessed portion of the reaction chamber 119B.

When the sample liquid 123 is transferred into the reaction chamber 119B in this state, the reagent set on the wall surface of the recessed portion of the reaction chamber 119B is hardly dissolved, so that an uneven color reaction may occur. Consequently, such a color reaction may become a major factor causing variations in measurement results. It is possible to suppress the contact of the reagent with the recessed portion of the reaction chamber 119B by sufficiently increasing the area of the reaction chamber 119B relative to the quantity of dropped reagent 122, however, the analyzing device increases in size and the quantity of sample liquid for analysis also increases.

Moreover, in this flow path configuration, the sample liquid 123 fully fills the reaction chamber 119B. Thus the sample liquid 123 has low flowability causing a long dissolving time of the reagent, and it takes a long time to evenly spread the dissolved reagent over the surface of the reaction chamber 119B, thereby disadvantageously increasing a measurement time and variations in measurement results.

An object of the present invention is to provide an analyzing device that enables measurement with a small quantity of sample liquid and makes it easy to reduce the size of an agitating mechanism, and an analyzing apparatus and an analyzing method using the analyzing device.

In patent document 3, a chamber structure made up of at least the quantifying chamber 333 and the reaction/detection chamber 334 is necessary for the quantification of the sample liquid, a reaction of the sample liquid with the reagent, and the detection of the sample liquid. Thus the quantification, reaction, and detection of the sample liquid cannot be performed in the same part.

In the case where the quantifying chamber 333 is so deep as to receive a capillary force and the quantification, reaction, and detection of the sample liquid are configured in the same part, the quantified sample liquid is sucked by the capillary force applied to the quantifying chamber 333 and is simultaneously discharged from the outlet 333c, so that the quantification of the sample liquid cannot be maintained.

An object of the present invention is to provide an analyzing device in which a sample liquid can be quantified and reacted with a reagent in the same part, and an analyzing method using the same.

Means for Solving the Problems

An analyzing device according to a first aspect of the present invention has a microchannel structure for transferring a sample liquid to measurement cells by a centrifugal force and is used for reading in which a reaction liquid of the sample liquid and a reagent is accessed in the measurement cells, wherein the measurement cell is formed so as to extend in a direction along which the centrifugal force is applied, the measurement cell has a capillary area that is formed on at least one of the side walls of the measurement cell so as to extend from the outer periphery position to the inner periphery of the measurement cell, the side walls being arranged in a rotational direction, and the sample liquid is sucked into the capillary area by a capillary force.

An analyzing device according to a second aspect of the present invention, in the first aspect, wherein the capillary area has a capacity large enough to fully accommodate the sample liquid retained in the measurement cell.

An analyzing device according to a third aspect of the present invention, in the first aspect, wherein the measurement cells are arranged in a circumferential direction.

An analyzing device according to a fourth aspect of the present invention, in the third aspect, wherein the measurement cells are arranged at an equal radius.

An analyzing device according to a fifth aspect of the present invention, in the first aspect, wherein the capillary area contains the reagent.

An analyzing apparatus according to a sixth aspect of the present invention has the analyzing device according to the first aspect set therein, the analyzing apparatus including: a rotational drive unit for rotating the analyzing device about an axis; a control unit for transferring the sample liquid into the measurement cells of the analyzing device by a rotation of the rotational drive unit; and an analyzing unit that accesses the reaction liquid of the sample liquid transferred into the measurement cells of the analyzing device by the rotation of the rotational drive unit and analyzes the reaction liquid, wherein the control unit is configured to transfer the sample liquid into the measurement cells of the analyzing device by the rotation of the rotational drive unit, suck the sample liquid of the measurement cells into the capillary areas formed on the at least one side walls of the measurement cells, and accelerate the rotation of the analyzing device such that the sample liquid sucked into the capillary areas is returned to the measurement cells and is agitated therein.

An analyzing method according to a seventh aspect of the present invention uses the analyzing device according to the first aspect, the analyzing method including: a first step of transferring the sample liquid to the measurement cells of the analyzing device by a centrifugal force generated by rotating the analyzing device; a second step of slowing or stopping the rotation of the analyzing device such that the sample liquid in the measurement cells is sucked by a capillary force into the capillary areas formed on the at least one side walls of the measurement cells, and then accelerating the rotation of the analyzing device such that the sample liquid sucked into the capillary areas is returned to the measurement cells and is agitated therein; and a third step of rotating the analyzing device and performing reading in which the reaction liquid of the sample liquid and the reagent is accessed when the measurement cell is located at a reading position.

An analyzing method according to an eighth aspect of the present invention, in the seventh aspect, wherein in the second step, the sample liquid is repeatedly sucked by the capillary force and the sample liquid in the capillary areas is repeatedly transferred to the outer peripheries of the measurement cells by the centrifugal force.

An analyzing device according to a ninth aspect of the present invention has a microchannel structure for transferring a sample liquid to measurement cells by a centrifugal force and is used for reading in which a reaction liquid of the sample liquid and a reagent is accessed in the measurement cells, wherein the measurement cell is formed so as to extend in a direction along which the centrifugal force is applied, the measurement cell has a capillary area that is formed on at least one of the side walls of the measurement cell so as to extend from the outer periphery position to the inner periphery of the measurement cell, the side walls being arranged in a rotational direction, and the reagent is disposed on a projecting portion formed on the capillary area.

An analyzing method according to a tenth aspect of the present invention uses an analyzing device that has a microchannel structure for transferring a sample liquid to measurement cells by a centrifugal force and is used for reading in which a reaction liquid of the sample liquid and a reagent is accessed in the measurement cells, the measurement cell being formed so as to extend in a direction along which the centrifugal force is applied, the measurement cell having a capillary area that is formed on at least one of the side walls of the measurement cell so as to extend from the outer periphery position to the inner periphery of the measurement cell, the side walls being arranged in a rotational direction, the capillary area containing the reagent, when a component of the sample liquid is analyzed from a detected value of light having passed through the sample liquid before the sample liquid reacts with the reagent and a detected value of light having passed through the sample liquid containing the dissolved reagent, the analyzing method including: rotating the analyzing device to supply the sample liquid to the outermost parts of the measurement cells and measuring, as a reference, the detected value of the light having passed through the sample liquid before the sample liquid reacts with the reagent; sucking the sample liquid into the capillary areas with a centrifugal force smaller than the centrifugal force applied to the sample liquid during reference measurement, and dissolving the reagent in the sample liquid; and applying the centrifugal force to the dissolved reagent contained in the capillary area, moving the reagent and the reacted sample liquid to the outermost part of the measurement cell, measuring the detected value of the light passing through the sample liquid, and comparing the detected value with the reference to analyze the component of the sample liquid.

An analyzing device according to an eleventh aspect of the present invention has a microchannel structure for transferring a sample liquid to measurement cells by a centrifugal force and is used for reading in which a reaction liquid of the sample liquid and a reagent is accessed in the measurement cells, wherein the measurement cell is formed so as to extend in a direction along which the centrifugal force is applied, the measurement cell has a capillary area formed so as to extend from the outer periphery position to the inner periphery of the measurement cell, the capillary area has one end, at the outer periphery position, connected to the side walls of the measurement cell, the side walls being arranged in a rotational direction, and at least a part of an area from the one end of the capillary area at the outer periphery position to the other end extending to the inner periphery is separated from the side walls of the measurement cell, the side walls being arranged in the rotational direction.

An analyzing device according to a twelfth aspect of the present invention, in the eleventh aspect, when the capillary area contains multiple reagents, the reagent having a higher viscosity is set outside the reagent having a lower viscosity.

An analyzing apparatus according to a thirteenth aspect of the present invention has the analyzing device according to the first aspect set therein, the analyzing apparatus including: a rotational drive unit for rotating the analyzing device about an axis; a control unit for transferring the sample liquid into the measurement cells of the analyzing device by a rotation of the rotational drive unit; and an analyzing unit for accessing the reaction liquid of the reagent and the sample liquid transferred into the measurement cells of the analyzing device by the rotation of the rotational drive unit and analyzing the reaction liquid, wherein the control unit is configured to transfer the sample liquid into the measurement cells of the analyzing device by the rotation of the rotational drive unit, suck the sample liquid of the measurement cells into the capillary areas while vibrating the analyzing device about the axis, and accelerate the rotation of the analyzing device such that the sample liquid sucked into the capillary areas is returned to the measurement cells and is agitated therein.

An analyzing method according to a fourteenth aspect of the present invention uses the analyzing device according to the eleventh aspect, the analyzing method including: a first step of transferring the sample liquid to the measurement cells of the analyzing device by a centrifugal force generated by rotating the analyzing device; a second step of vibrating the analyzing device such that the analyzing device swings so as to laterally reciprocate at a predetermined stop position with respect to a rotation axis, sucking the sample liquid transferred to the measurement cells to the capillary areas by a capillary force, and then accelerating the rotation of the analyzing device such that the sample liquid sucked into the capillary areas is returned to the measurement cells and is agitated therein; and a third step of rotating the analyzing device and performing reading in which the reaction liquid of the sample liquid and the reagent is accessed in the measurement cell when the measurement cell is located at a reading position.

An analyzing device according to a fifteenth aspect of the present invention is rotationally driven about a rotation axis to control the transfer of a liquid in the analyzing device, the analyzing device including: a sample retaining part for receiving a sample liquid, the sample retaining part being connected to a connection port on one side wall of the inner periphery of a sample quantifying capillary, in which the sample liquid is quantified and reacted with a reagent, with respect to the rotation axis via a capillary siphon formed toward the rotation axis; and a sample photometric part for measuring the sample liquid reacted with the reagent, the sample photometric part being provided on the outer periphery of the sample quantifying capillary with respect to the rotation axis, wherein a flow velocity V1 for sucking the liquid along the one side wall is lower than a flow velocity V2 for sucking the liquid along the other side wall separated from the connection port, in the sample quantifying capillary to which the liquid is sucked by a capillary force, the liquid having been transferred from the sample quantifying capillary to the sample photometric part by a centrifugal force generated by rotational driving.

An analyzing device according to a sixteenth aspect of the present invention, in the fifteenth aspect, further including a first recessed portion surrounding the sample quantifying capillary, wherein the sample quantifying capillary includes a second recessed portion formed along the side wall close to the connection port, and a projecting portion formed along the side wall separated from the connection port, the second recessed portion being deeper than the sample quantifying capillary.

An analyzing device according to a seventeenth aspect of the present invention, in the fifteenth aspect, wherein the sample quantifying capillary contains the reagent to be reacted with the sample liquid.

An analyzing method according to an eighteenth aspect of the present invention, including: injecting a sample liquid to be analyzed, into the sample retaining part of the analyzing device according to the fifteenth aspect; repeatedly rotating and stopping the analyzing device; and mixing and agitating the sample liquid and the reagent in the sample quantifying capillary by a centrifugal force generated by rotating the analyzing device and a capillary force in the sample quantifying capillary of the analyzing device.

An analyzing method according to a nineteenth aspect of the present invention, in the eighteenth aspect, wherein the centrifugal force is generated at rpm where the centrifugal force applied to the sample liquid transferred to the sample quantifying capillary is larger than the capillary force.

Advantage of the Invention

According to an analyzing device, an analyzing apparatus using the same, and an analyzing method according to the present invention, a measurement cell is formed so as to extend in a centrifugal direction (from the outer periphery position to the inner periphery of the measurement cell). Thus a required quantity of a sample liquid for measurement can be determined at a liquid level filling a light irradiation area for optical measurement and with the minimum measurement cell width, so that a measurement can be conducted with the minimum liquid volume. Further, a capillary area provided in the measurement cell can eliminate an unnecessary space, thereby reducing the size of the analyzing device.

According to the configuration of the present invention, a sample retaining part for receiving a sample liquid is connected to a connection port on one side wall of the inner periphery of a sample quantifying capillary, in which the sample liquid is quantified and reacted with a reagent, with respect to a rotation axis via a capillary siphon formed toward the rotation axis; and a sample photometric part for measuring the sample liquid reacted with the reagent is provided on the outer periphery of the sample quantifying capillary with respect to the rotation axis, and a flow velocity V1 for sucking the liquid along the one side wall is lower than a flow velocity V2 for sucking the liquid along the other side wall separated from the connection port, in the sample quantifying capillary to which the liquid having been transferred from the sample quantifying capillary to the sample photometric part is sucked by a centrifugal force generated by rotational driving. Thus the sample liquid can be quantified and reacted with the reagent in the same part.

BEST MODE FOR CARRYING OUT THE INVENTION

First Embodiment

FIGS. 1(a) and 1(b) show an analyzing device 1 with an opened and closed protective cap 2. FIG. 2 is an exploded view of the analyzing device 1 with the underside of FIG. 1(a) placed face up. FIG. 3 is an assembly drawing of FIG. 2.

Figure 1:
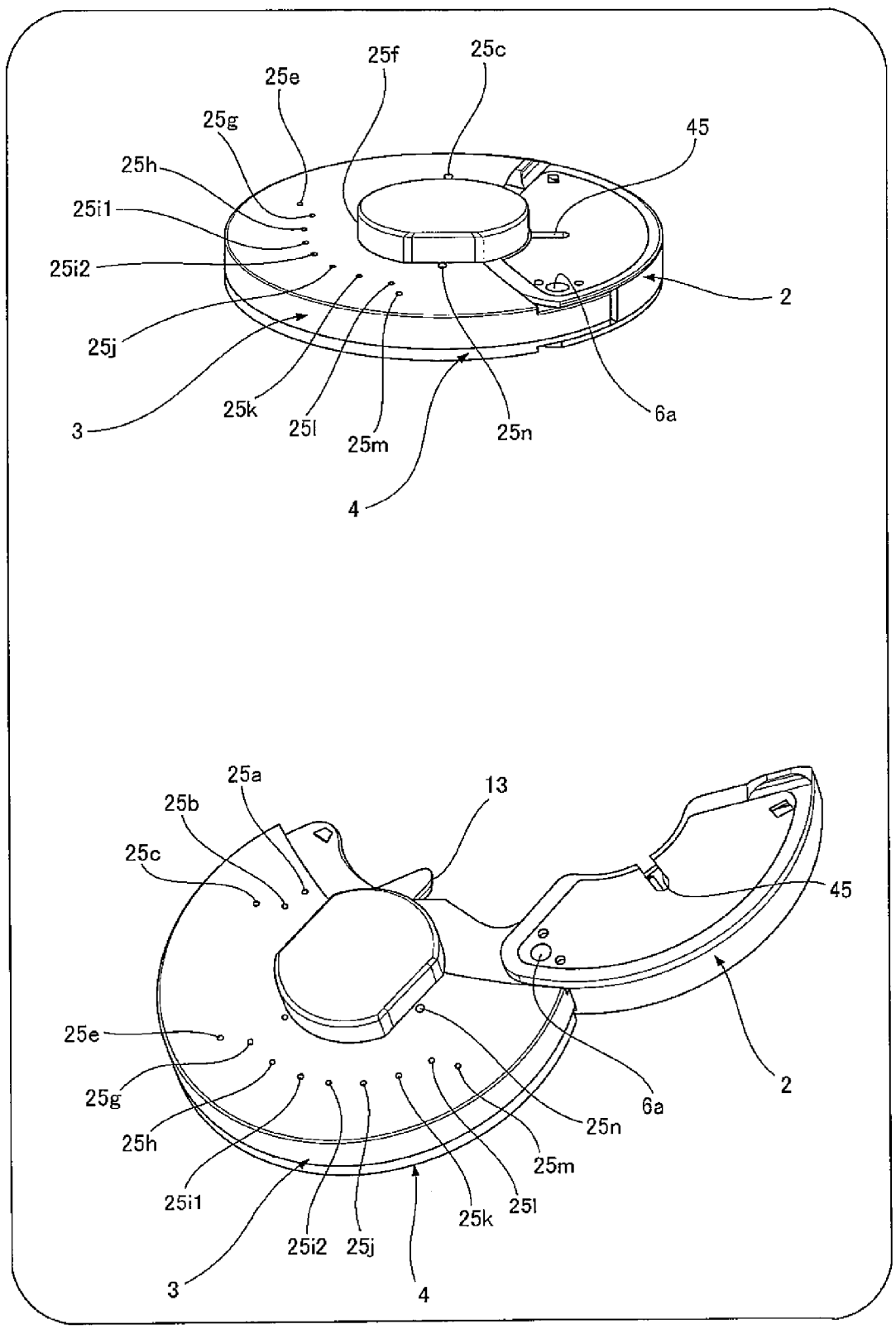
FIG. 1 is an outside perspective view showing an analyzing device with an opened and closed protective cap according to a first embodiment of the present invention.
Figure 2:
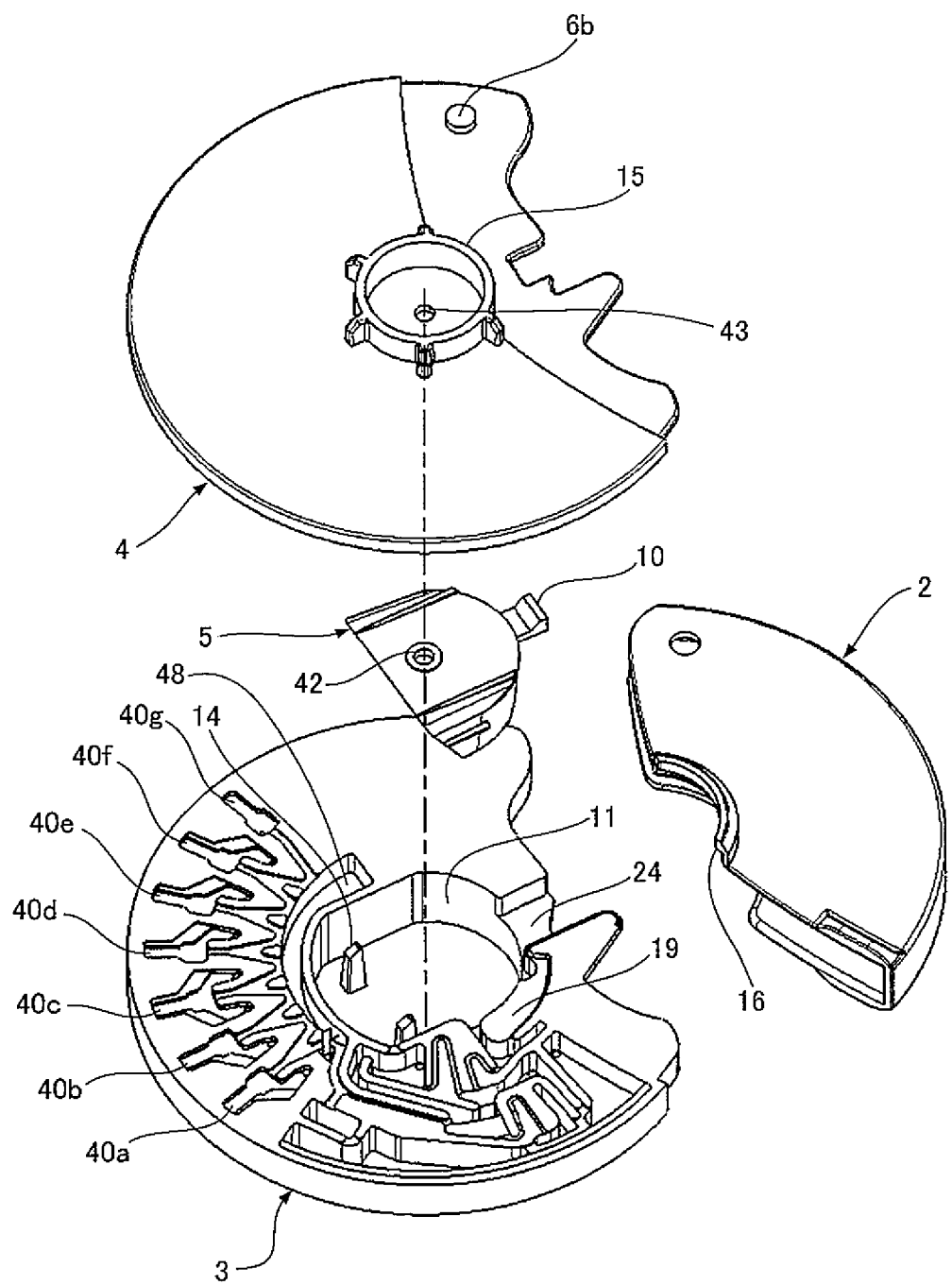
FIG. 2 is an exploded perspective view showing the analyzing device of the first embodiment.
Figure 3:
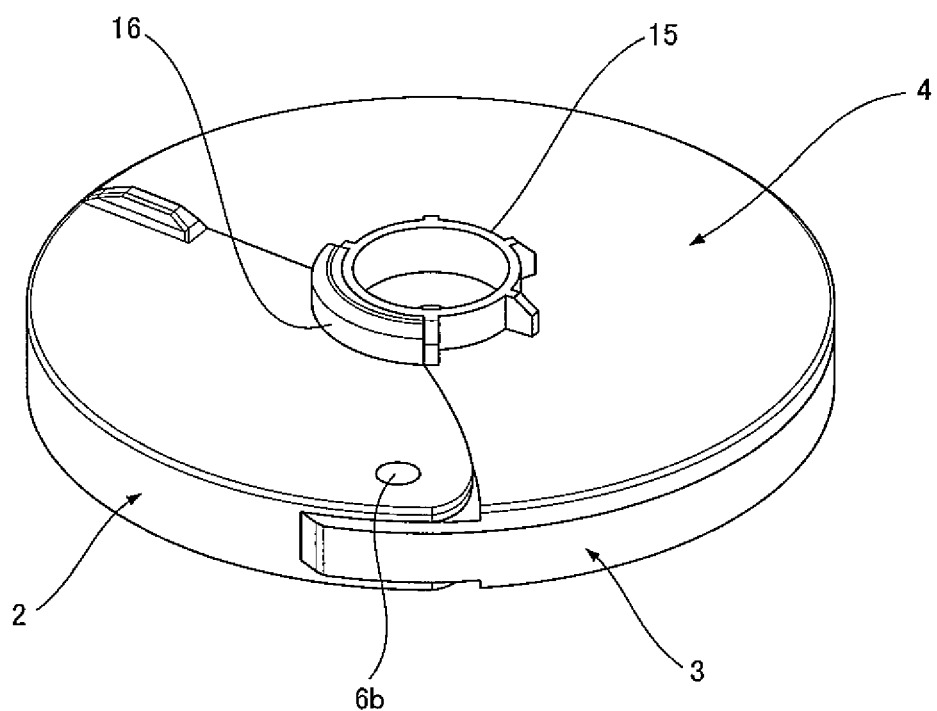
FIG. 3 is a perspective view showing the rear of the analyzing device with the closed protective cap.

As shown in FIGS. 1 and 2, the analyzing device is made up of four components of a base substrate 3 having a microchannel structure formed on one surface, the microchannel structure having a minutely uneven surface, a cover substrate 4 covering the surface of the base substrate 3, a diluent container 5 for retaining a diluent, and the protective cap 2 for preventing splashes of a sample liquid.

The base substrate 3 and the cover substrate 4 are joined to each other with the diluent container 5 and so on set in the base substrate 3 and the cover substrate 4, and the protective cap 2 is attached to the joined base substrate 3 and cover substrate 4.

The cover substrate 4 covers the openings of several recessed portions formed on the top surface of the base substrate 3, thereby forming a plurality of storage areas, which will be described later (like measurement cells that will be describe later), the passages of the microchannel structure connecting the storage areas, and so on. In necessary ones of the storage areas, reagents required for various analyses are set beforehand. One side of the protective cap 2 is pivotally supported such that the protective cap 2 can be opened and closed in engagement with shafts 6a and 6b formed on the base substrate 3 and the cover substrate 4. When a sample liquid to be inspected is blood, the passages of the microchannel structure receiving a capillary force have clearances of 50 µm to 300 µm.

The outline of an analyzing process using the analyzing device 1 is that a sample liquid is dropped into the analyzing device 1 in which the diluent has been set, at least a part of the sample liquid is diluted with the diluent, and then a measurement is conducted.

Figure 4:
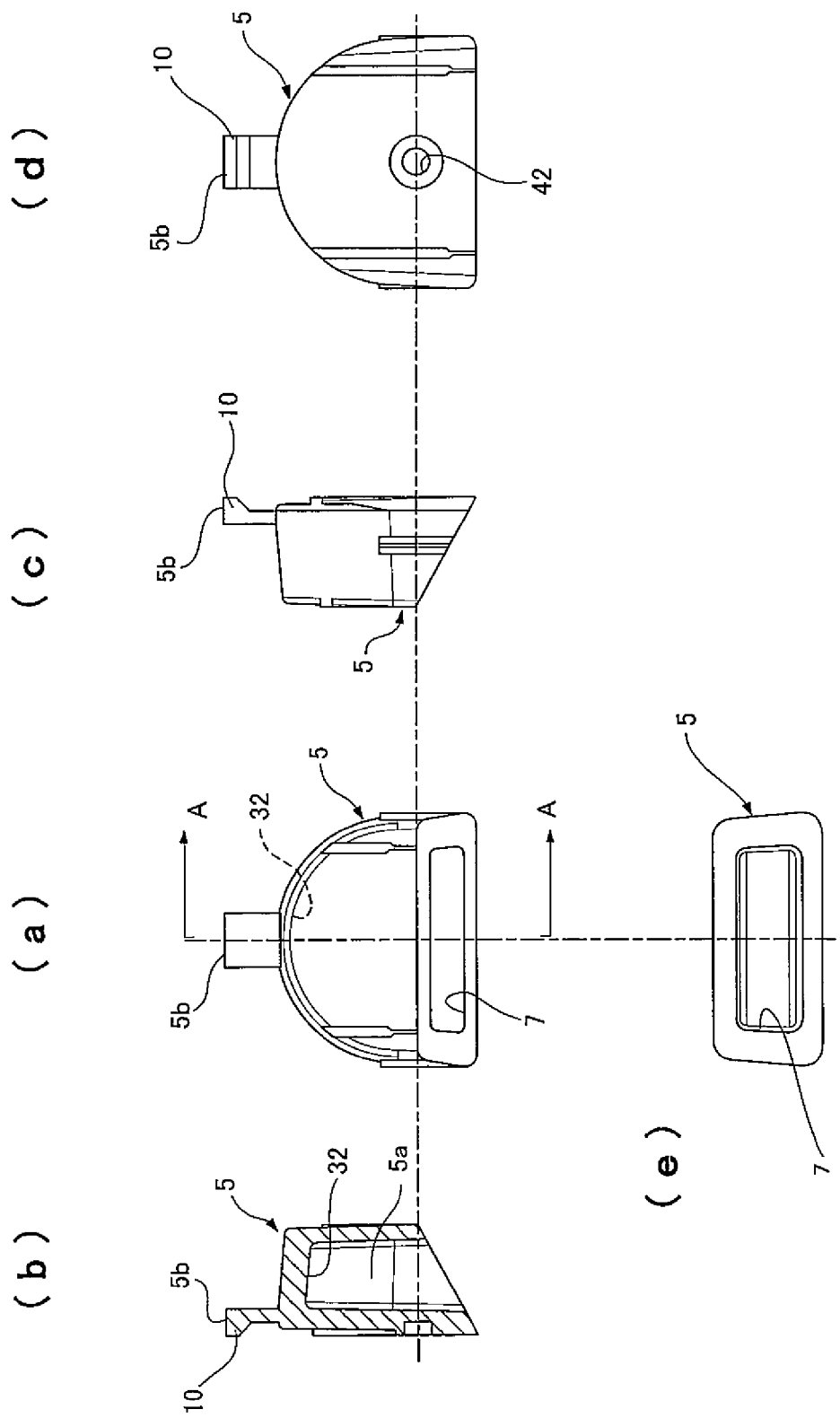
FIG. 4 is an explanatory drawing showing a diluent container according to the first embodiment.

FIG. 4 shows the shape of the diluent container 5.

Figure 6:
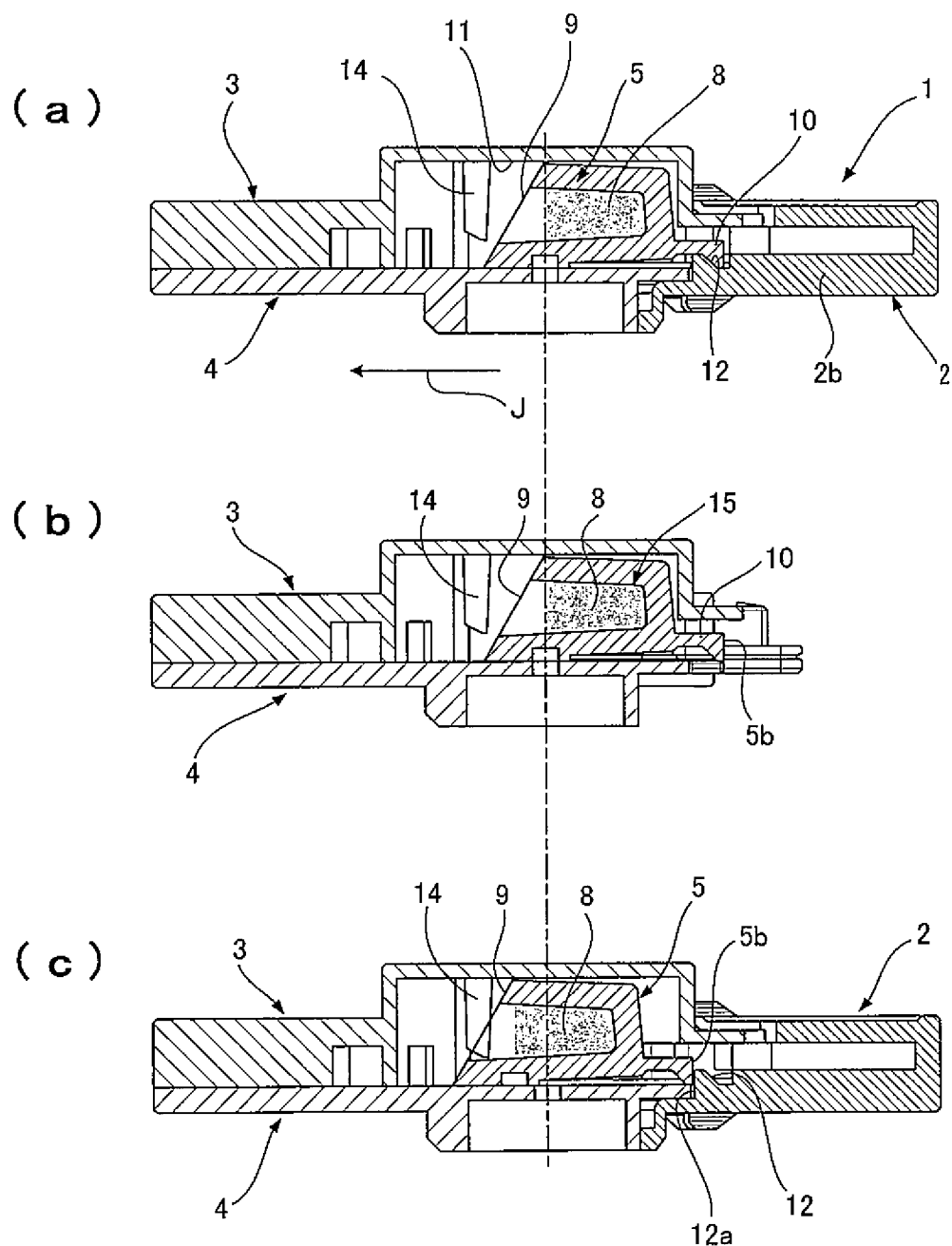
FIG. 6 is a sectional view showing a state before the analyzing device is used, a state at the dropping of a sample liquid, and a state in which the protective cap is closed after the sample liquid is dropped.

FIG. 4(a) is a plan view, FIG. 4(b) is an A-A sectional view of FIG. 4(a), FIG. 4(c) is a side view, FIG. 4(d) is a rear view, and FIG. 4(e) is a front view taken from an opening 7. After an interior 5a of the diluent container 5 is filled with a diluent 8 as shown in FIG. 6(a), the opening 7 is enclosed with an aluminum seal 9 serving as a sealing member. On the opposite side of the diluent container 5 from the opening 7, a latch portion 10 is formed. The diluent container 5 is set in a diluent container storage part 11 formed between the base substrate 3 and the cover substrate 4, and is accommodated movably between a liquid retaining position shown in FIG. 6(a) and a liquid discharging position shown in FIG. 6(c).

Figure 5:
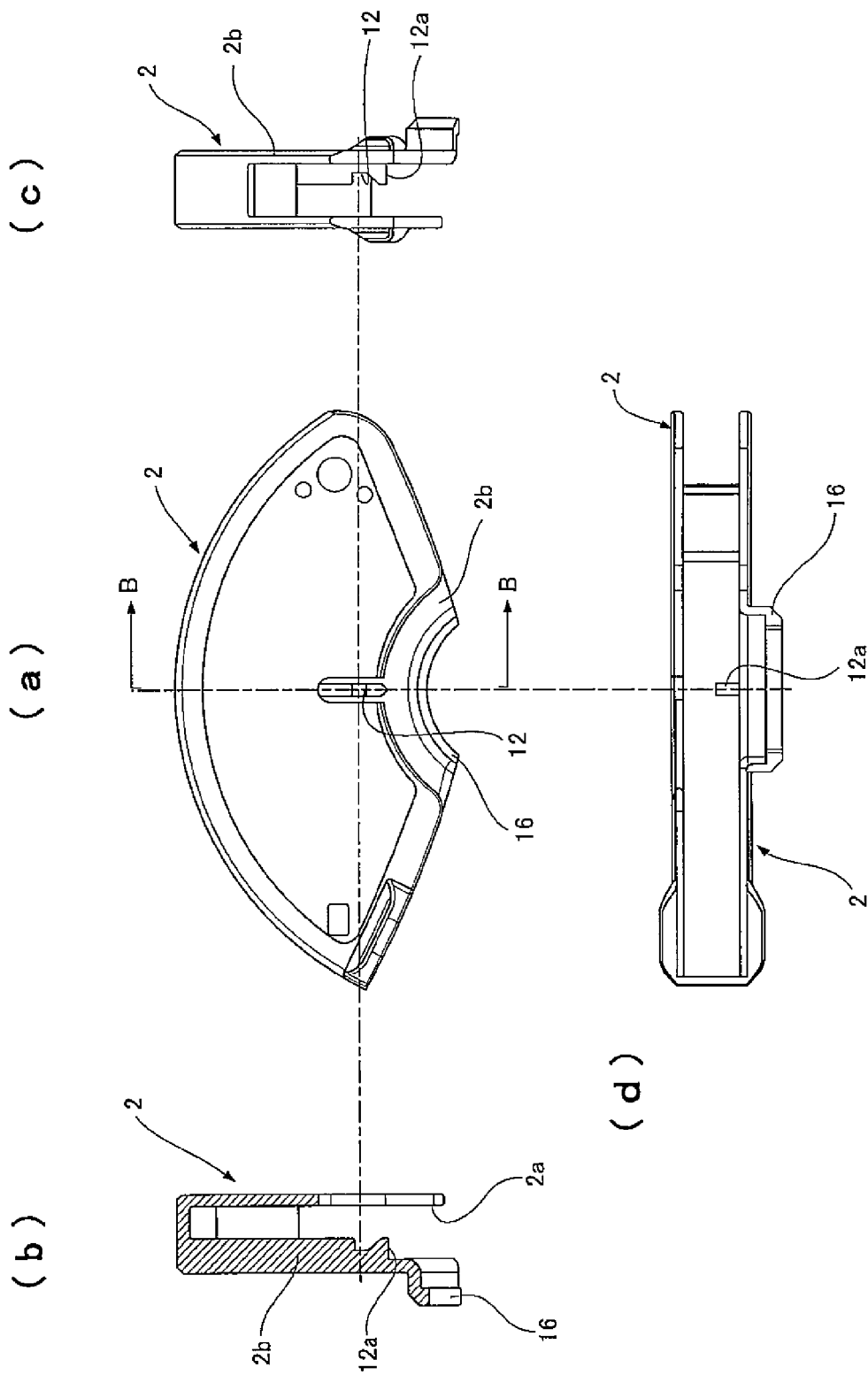
FIG. 5 is an explanatory drawing showing the protective cap of the first embodiment.

FIG. 5 shows the shape of the protective cap 2.

FIG. 5(a) is a plan view, FIG. 5(b) is a B-B sectional view of FIG. 5(a), FIG. 5(c) is a side view, and FIG. 5(d) is a front view taken from an opening 2a. In the protective cap 2, a locking groove 12 is formed. In the closed state of FIG. 1(a), the latch portion 10 of the diluent container 5 can be engaged with the locking groove 12 as shown in FIG. 6(a).

FIG. 6(a) shows the analyzing device 1 before use. In this state, the protective cap 2 is closed and the latch portion 10 of the diluent container 5 is engaged with the locking groove 12 of the protective cap 2 to lock the diluent container 5 at the liquid retaining position, so that the diluent container 5 does not move in the direction of arrow J. The analyzing device 1 in this state is supplied to a user.

When the sample liquid is dropped, the protective cap 2 is opened as shown in FIG. 1(b) against the engagement with the latch portion 10 in FIG. 6(a). At this point, a bottom 2b of the protective cap 2 is elastically deformed with the locking groove 12 formed on the bottom 2b, thereby disengaging the latch portion 10 of the diluent container 5 from the locking groove 12 of the protective cap 2 as shown in FIG. 6(b).

In this state, the sample liquid is dropped to an exposed inlet 13 of the analyzing device 1 and then the protective cap 2 is closed. At this point, by closing the protective cap 2, a wall surface 12a forming the locking groove 12 comes into contact with a surface 5b of the latch portion 10 of the diluent container 5 on the protective cap 2, and the wall surface 12a presses the diluent container 5 in the direction of arrow J (a direction that comes close to the liquid discharging position). The diluent container storage part 11 has an opening rib 14 formed therein as a portion projecting from the base substrate 3. When the diluent container 5 is pressed by the protective cap 2, the aluminum seal 9 provided on the inclined seal face of the opening 7 of the diluent container 5 is collided with and broken by the opening rib 14 as shown in FIG. 6(c).

Figure 7:
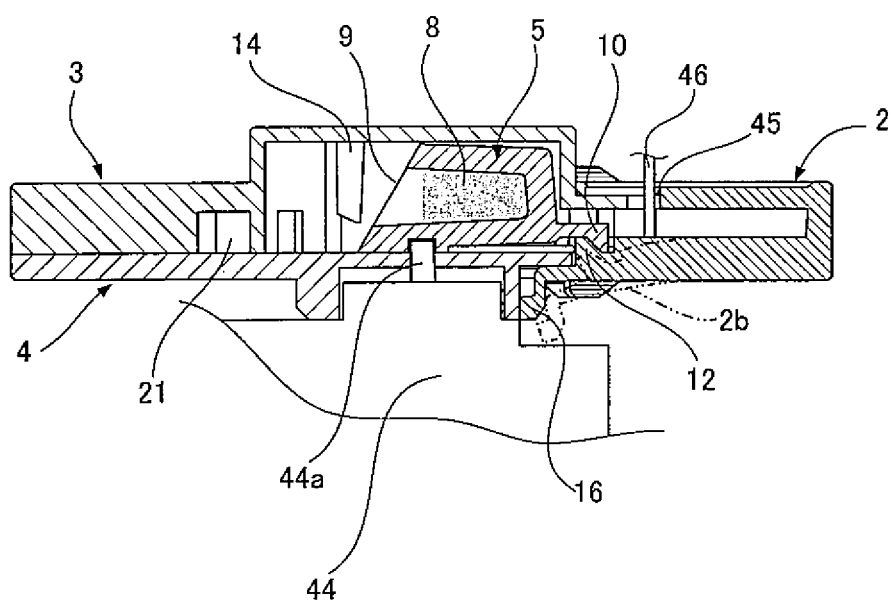
FIG. 7 is a sectional view showing a process of setting the analyzing device at a shipment state.

FIG. 7 shows a manufacturing process for setting the analyzing device 1 at the shipment state of FIG. 6(a). First, before the protective cap 2 is closed, a groove 42 (see FIGS. 2(b) and 4(d)) provided on the undersurface of the diluent container 5 and a hole 43 provided on the cover substrate 4 are aligned with each other, and a projecting portion 44a of a locking member 44 is engaged with the groove 42 of the diluent container 5 through the hole 43 at the liquid retaining position. The projecting portion 44a is provided separately from the base substrate 3 or the cover substrate 4. The diluent container 5 is set so as to be locked at the liquid retaining position. Further, from a notch 45 (see FIG. 1) formed on the top surface of the protective cap 2, a pressing member 46 is inserted and presses the bottom of the protective cap 2 to elastically deform the protective cap 2. In this state, the protective cap 2 is closed and then the pressing member 46 is removed, so that the analyzing device 1 can be set in the state of FIG. 6(a).

The first embodiment described an example in which the groove 42 is provided on the undersurface of the diluent container 5. The groove 42 may be provided on the top surface of the diluent container 5 and the hole 43 may be provided on the base substrate 3 in alignment with the groove 42 so as to engage the projecting portion 44a of the locking member 44 with the groove 42.

In the present embodiment, the locking groove 12 of the protective cap 2 is directly engaged with the latch portion 10 of the diluent container 5 to lock the diluent container 5 at the liquid retaining position. The locking groove 12 of the protective cap 2 and the latch portion 10 of the diluent container 5 may be indirectly engaged with each other to lock the diluent container 5 at the liquid retaining position.

Figure 8:
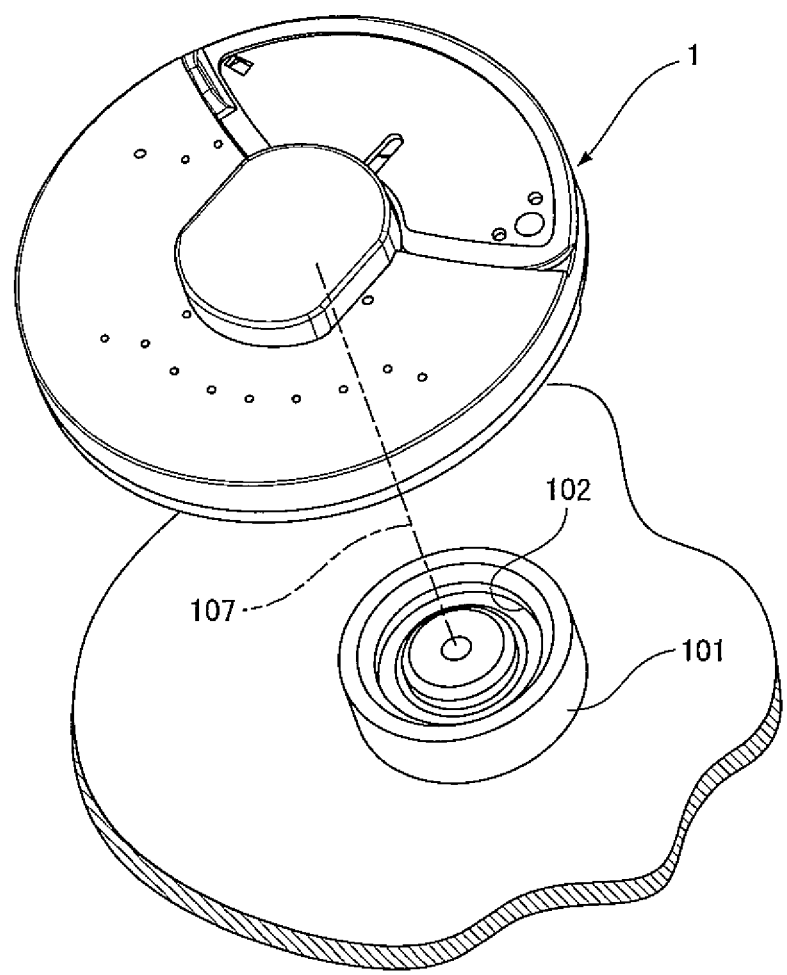
FIG. 8 is a perspective view showing a state immediately before the analyzing device is set in an analyzing apparatus.
Figure 9:
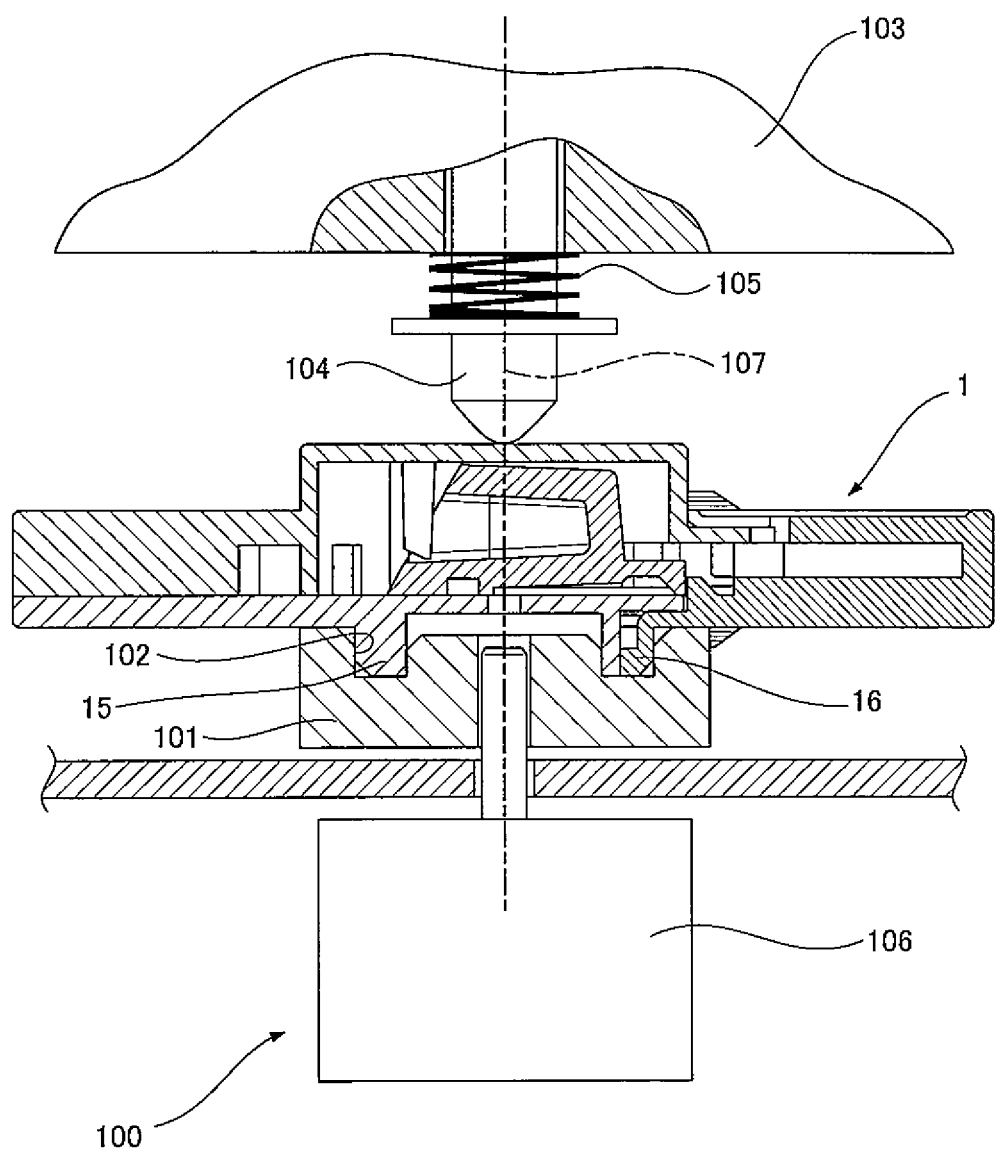
FIG. 9 is a sectional view showing a state in which the analyzing device is set in the analyzing apparatus.

As shown in FIGS. 8 and 9, the analyzing device 1 is set on a rotor 101 of an analyzing apparatus 100 with the cover substrate 4 placed on the underside of the analyzing device 1, so that a component of the sample liquid can be analyzed.

On the top surface of the rotor 101, a groove 102 is formed. In a state in which the analyzing device 1 is set on the rotor 101, a rotary support part 15 formed on the cover substrate 4 of the analyzing device 1 and a rotary support part 16 formed on the protective cap 2 are engaged with the groove 102, so that the analyzing device 1 is accommodated.

After the analyzing device 1 is set on the rotor 101, a door 103 of the analyzing apparatus is closed before a rotation of the rotor 101, so that the set analyzing device 1 is pressed to the rotor 101 by a movable piece 104 provided on the door 103, by a biasing force of a spring 105 at a position on the rotation axis of the rotor 101. The analyzing device 1 rotates along with the rotor 101 that is rotationally driven by a rotational drive unit 106. Reference numeral 107 denotes the axis of rotation of the rotor 101. The protective cap 2 is attached to prevent the sample liquid deposited around the inlet 13 from being splashed to the outside by a centrifugal force during analysis.

The components constituting the analyzing device 1 are desirably made of resin materials enabling low material cost with high mass productivity. The analyzing apparatus 100 analyzes the sample liquid according to an optical measurement method for measuring light having passed through the analyzing device 1. Thus the base substrate 3 and the cover substrate 4 are desirably made of transparent synthetic resins including PC, PMMA, AS, and MS.

The diluent container 5 is desirably made of crystalline synthetic resins such as PP and PE that have low moisture permeability. This is because the diluent container 5 has to contain the diluent 8 for a long period. The protective cap 2 may be made of any materials as long as high moldability is obtained. Inexpensive resins such as PP and PE are desirable.

The base substrate 3 and the cover substrate 4 are desirably joined to each other according to a method hardly affecting the reaction activity of a reagent retained in the storage area. Thus methods such as ultrasonic welding and laser welding are desirable by which reactive gas and solvent are hardly generated during joining.

On a portion where a solution is transferred by a capillary force in a small clearance between the base substrate 3 and the cover substrate 4 that are joined to each other, hydrophilic treatment is performed to increase the capillary force. To be specific, hydrophilic treatment is performed using a hydrophilic polymer, a surface-active agent, and so on. In this case, hydrophilicity is a state in which a contact angle is less than 90° relative to water. More preferably, the contact angle is less than 40°.

Figure 10:
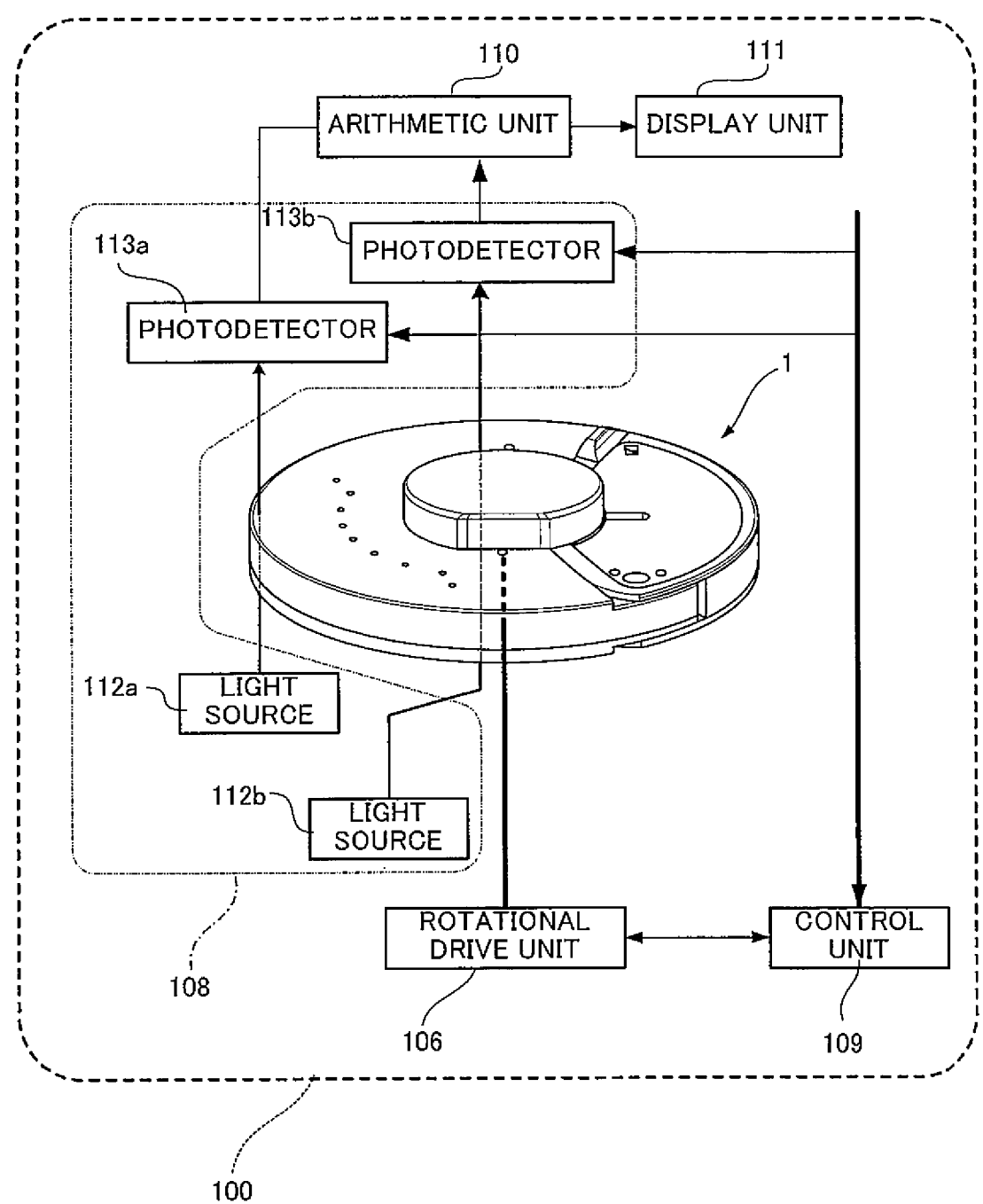
FIG. 10 is a structural diagram showing the analyzing apparatus of the first embodiment.

FIG. 10 shows the configuration of the analyzing apparatus 100.

The analyzing apparatus 100 is made up of the rotational drive unit 106 for rotating the rotor 101; an optical measurement unit 108 for accessing a reactant in the analyzing device 1 and analyzing the reactant; a control unit 109 for controlling the rotation speed and direction of the rotor 101, the measurement timing of the optical measurement unit 108, and so on; an arithmetic unit 110 for calculating a measurement result by processing a signal obtained by the optical measurement unit 108; and a display unit 111 for displaying the result obtained by the arithmetic unit 110.

The rotational drive unit 106 can rotate the analyzing device 1 through the rotor 101 about a rotation axis 107 in any direction at a predetermined rotation speed and can further vibrate the analyzing device 1 such that the analyzing device 1 laterally reciprocates at a predetermined stop position with respect to the rotation axis 107 with a predetermined amplitude range and a predetermined period.

The optical measurement unit 108 includes a light source 112a for emitting light to the measurement cell of the analyzing device 1; a photodetector 113a for detecting the quantity of light having passed through the analyzing device 1 out of the light emitted from the light source 112a; a light source 112b for emitting light to a measured part other than the measurement cell of the analyzing device 1; and a photodetector 113b for detecting the quantity of light having passed through the analyzing device 1 out of the light emitted from the light source 112b.

The analyzing device 1 is rotationally driven by the rotor 101, and the sample liquid drawn into the analyzing device 1 from the inlet 13 is transferred in the analyzing device 1 by using a centrifugal force generated by rotating the analyzing device 1 about the rotation axis 107 located inside the inlet 13 and the capillary force of a capillary passage provided in the analyzing device 1. The microchannel structure of the analyzing device 1 will be specifically described below along with an analyzing process.

Figure 11A:
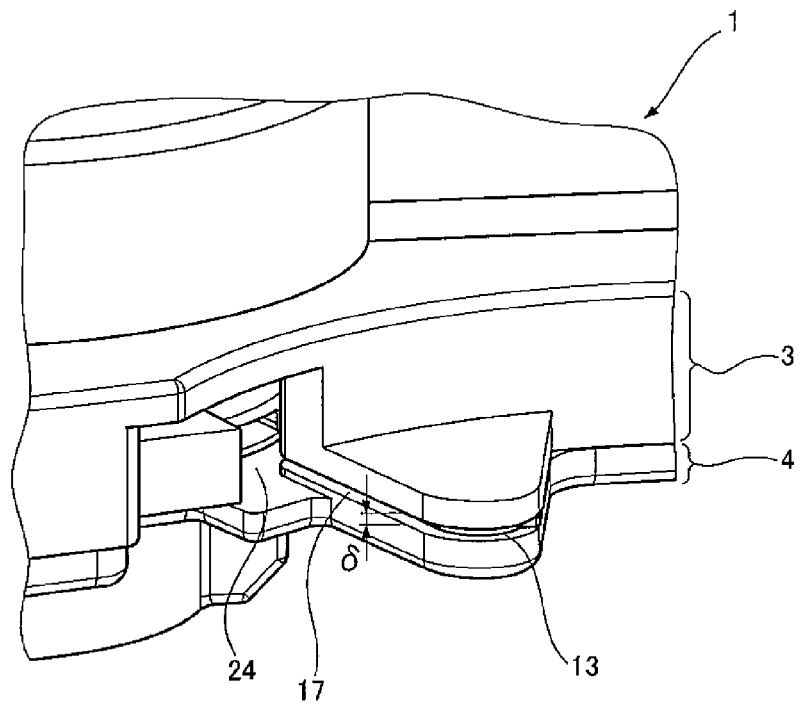
FIG. 11A is an enlarged perspective view showing a part around the inlet of the analyzing device according to the first embodiment.
Figure 11B:
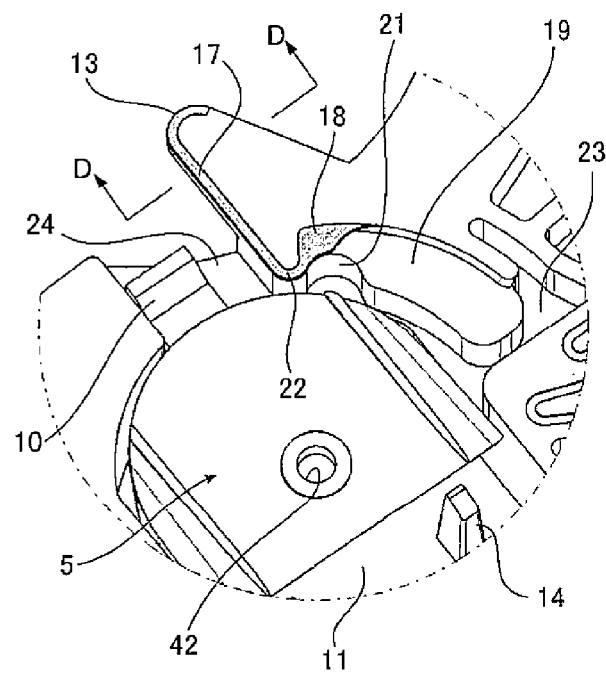
FIG. 11B is an enlarged perspective view showing the part around the inlet through the cover substrate.
Figure 11C:
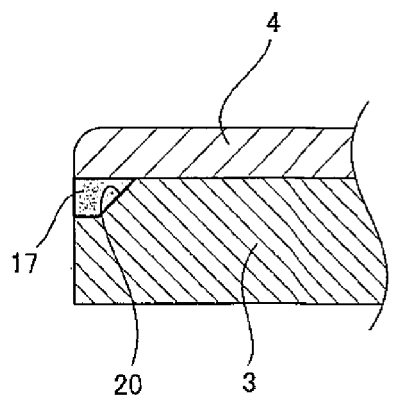
FIG. 11C is a D-D sectional view of FIG. 11B.

FIGS. 11A, 11B and 11C show a portion around the inlet 13 of the analyzing device 1.

FIG. 11A is an enlarged view showing the inlet 13 from the outside of the analyzing device 1. FIG. 11B is a perspective view showing the microchannel structure from the rotor 101 through the cover substrate 4.

The inlet 13 is connected to a capillary cavity 19 through a guide portion 17 receiving a capillary force with a small clearance 8 formed between the base substrate 3 and the cover substrate 4. The capillary cavity 19 has a capacity large enough to retain a required quantity of a sample liquid 18 with a clearance that receives a capillary force as in the guide portion 17. The cross section of the guide portion 17 (cross section D-D in FIG. 11B) in an orthogonal direction to a flow direction shows that the rear of the guide portion 17 is not an upright rectangle. As shown in FIG. 11C, the guide portion 17 is formed of an inclined surface 20 such that the rear end of the guide portion 17 gradually narrows toward the cover substrate 4. On the guide portion 17, the capillary cavity 19, and the joint, a bending portion 22 is formed that changes the direction of a passage with a recessed portion 21 formed on the base substrate 3.

When viewed from the guide portion 17, a sample liquid receiving cavity 23 having a clearance not large enough to receive a capillary force is formed behind the capillary cavity 19. Partially on the sides of the capillary cavity 19, the bending portion 22, and the guide portion 17, a cavity 24 is formed that has one end connected to the sample liquid receiving cavity 23 and the other end opened to the atmosphere.

Figure 12:
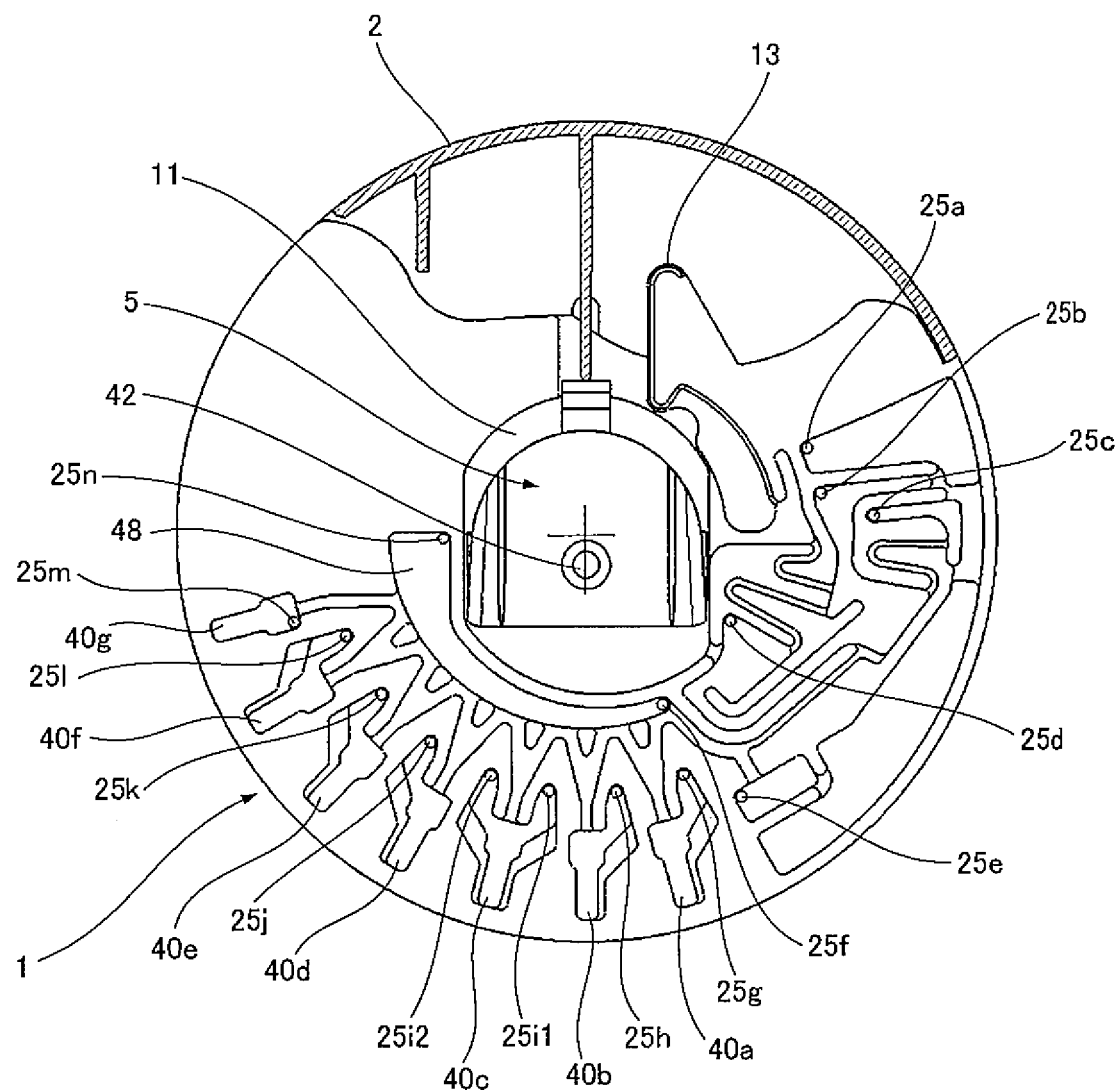
FIG. 12 is a sectional view showing the analyzing device set in the analyzing apparatus before the start of rotation.

With this configuration, blood dropped as the sample liquid 18 to the inlet 13 is drawn to the capillary cavity 19 through the guide portion 17. FIG. 12 shows a state before the analyzing device 1 containing the dropped sample liquid 18 is set on the rotor 101 and is rotated thereon. At this point, as shown in FIG. 6(c), the aluminum seal 9 of the diluent container 5 has been collided with the opening rib 14 and broken by the opening rib 14. Reference characters 25a to 25g, 25h, 25i1, 25i2, and 25j to 25n denote air holes formed on the base substrate 3.

The following will describe the analyzing process along with the configuration of the control unit 109 that controls the operation of the rotational drive unit 106.

Step 1

Figure 13A:
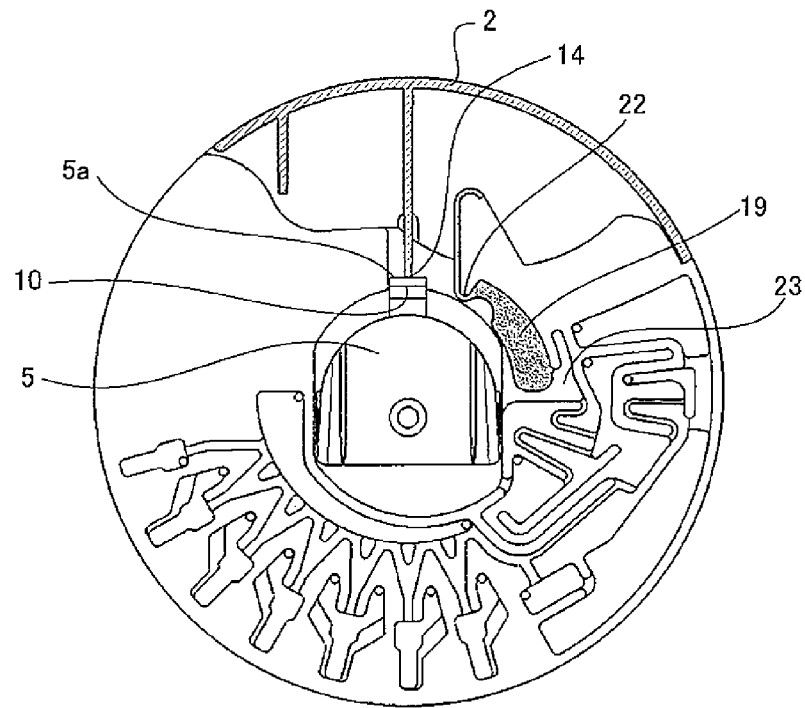
FIG. 13A is a sectional view showing the analyzing device before centrifugal separation.

As shown in FIG. 13A, the analyzing device 1 in which the sample liquid to be inspected has been dropped into the inlet 13 is set on the rotor 101 in a state in which the sample liquid is retained in the capillary cavity 19 and the aluminum seal 9 of the diluent container 5 has been broken.

Step 2

Figure 13B:
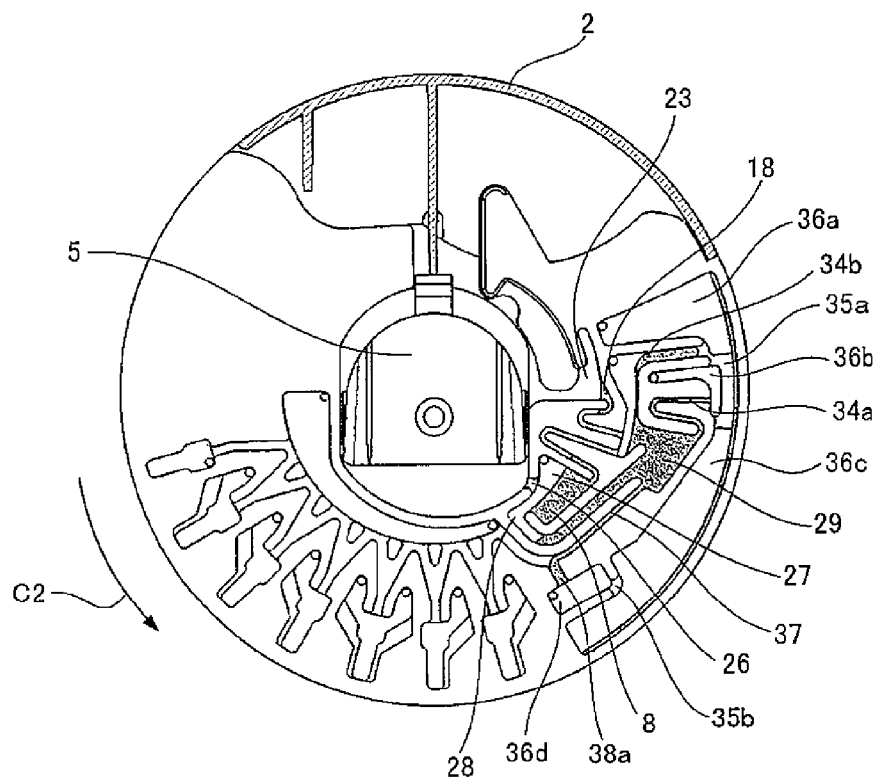
FIG. 13B is a sectional view showing the analyzing device after centrifugal separation.

The door 103 is closed and then the rotor 101 is rotationally driven in a clockwise direction (direction C2), so that the retained sample liquid overflows at the position of the bending portion 22. The sample liquid in the guide portion 17 is discharged into the protective cap 2, and the sample liquid 18 in the capillary cavity 19 flows into the sample liquid receiving cavity 23 and is retained therein as shown in FIG. 13B.

The diluent 8 from the diluent container 5 flows into a retaining cavity 27 through a discharging passage 26. When the diluent 8 having flowed into the retaining cavity 27 exceeds a predetermined quantity, as shown in FIG. 13B, the excessive quantity of the diluent 8 flows into a mixing cavity 29 through an overflow passage 28. When the diluent 8 having flowed into the mixing cavity 29 exceeds a predetermined quantity, the excessive quantity of the diluent 8 flows into overflow cavities 36a, 36b, 36c, and 36d through connecting passages 34a and 34b and an overflow passage 38. The diluent 8 having flowed into the overflow cavities 36a, 36b, and 36c is retained in the overflow cavities 36a, 36b, and 36c by the capillary forces of backflow preventing passages 35a and 35b.

In this configuration, the diluent 8 is a solution having a specified absorbance in a specific wave range. The absorbance of the diluent 8 is measured (primary photometry) while the diluent 8 having flowed into the mixing cavity 29 is retained in the mixing cavity 29. To be specific, when the analyzing device 1 is rotationally driven in the clockwise direction (direction C2) and the mixing cavity 29 containing the diluent 8 passes between the light source 112b and the photodetector 113b, the arithmetic unit 110 reads a detected value of the photodetector 113b.

The connecting passage 34a has a siphon structure including a bending portion formed from the outermost part to the inner periphery of the mixing cavity 29. When the diluent 8 exceeds the bending portion of the connecting passage 34a, the diluent 8 in the mixing cavity 29 is discharged into the overflow cavities 36a, 36b, and 36c by a siphon action. Further, by providing the connecting passage 34b inside the connecting passage 34a to discharge the diluent exceeding the predetermined quantity, it is possible to prevent the excessive diluent from flowing into the sample liquid receiving cavity 23 from the mixing cavity 29.

Figure 14A:
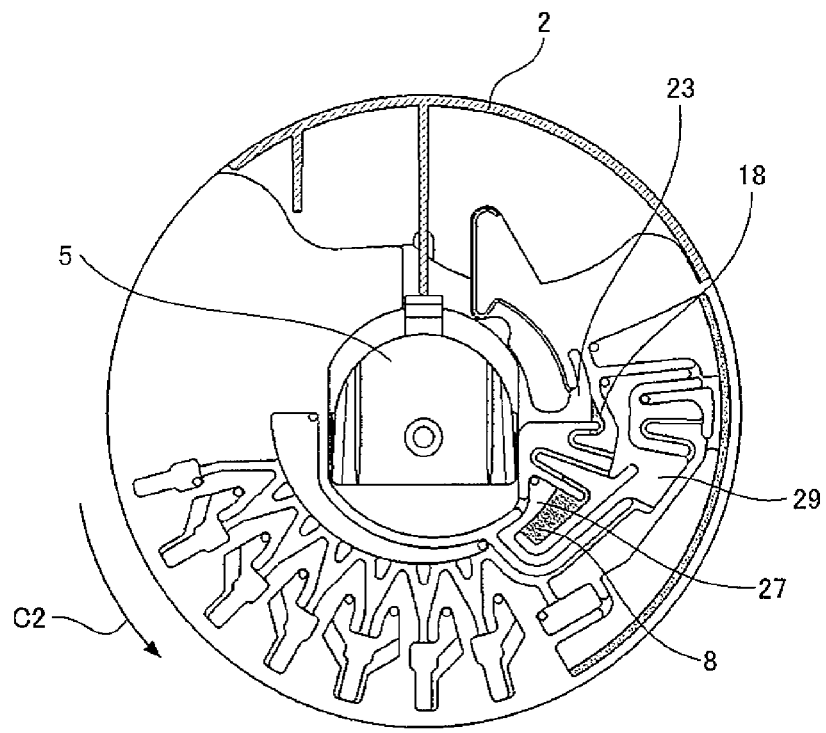
FIG. 14A is a sectional view showing the sample liquid and a diluent are retained in a sample liquid receiving cavity 23 and a retaining cavity 27.

The diluent 8 retained in the mixing cavity 29 is completely discharged to the overflow cavities 36a, 36b, and 36c with the passage of time. As shown in FIG. 14A, a predetermined quantity of the sample liquid 18 and a predetermined quantity of the diluent 8 are retained in the sample liquid receiving cavity 23 and the retaining cavity 27, respectively.

Figure 15:
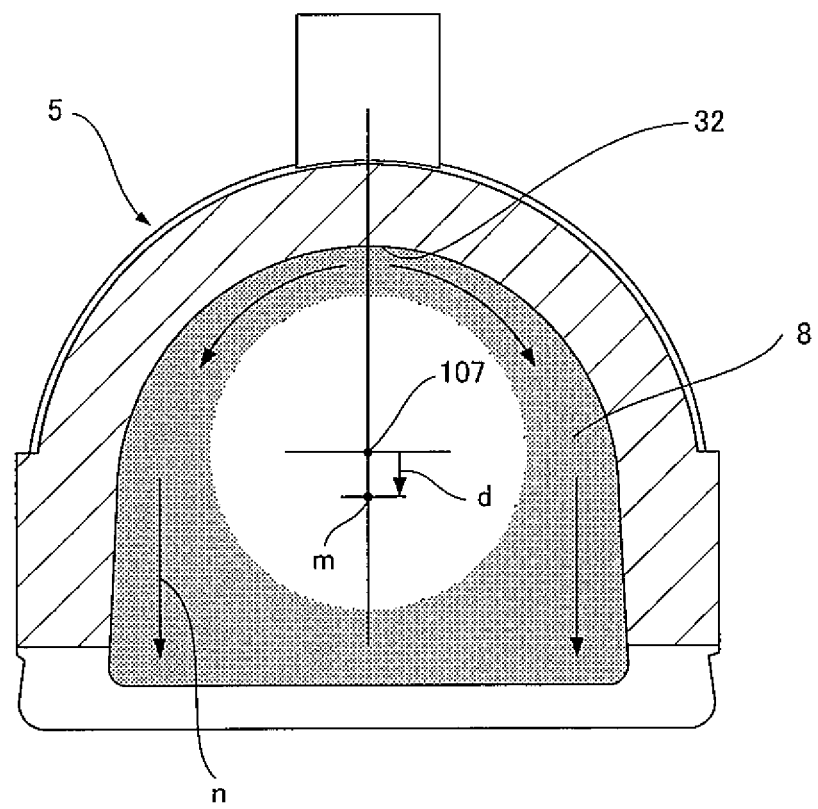
FIG. 15 is a sectional view showing the rotation axis of the analyzing device and the diluent container when the diluents is discharged from the diluent container.

As shown in FIGS. 4(a) and 4(b), the bottom of the diluent container 5 on the opposite side from the opening 7 sealed with the aluminum seal 9 is formed of a curved surface 32. At the liquid discharging position of the diluent container 5 in the state of FIG. 13B, a center m of the curved surface 32 is offset, as shown in FIG. 15, by a distance d from the rotation axis 107 to the discharging passage 26. The diluent 8 having flowed to the curved surface 32 is changed to a flow (arrow n) directed from the outside to the opening 7 along the curved surface 32, and the diluent 8 is efficiently discharged to the diluent container storage part 11 from the opening 7 of the diluent container 5.

Step 3

Figure 14B:
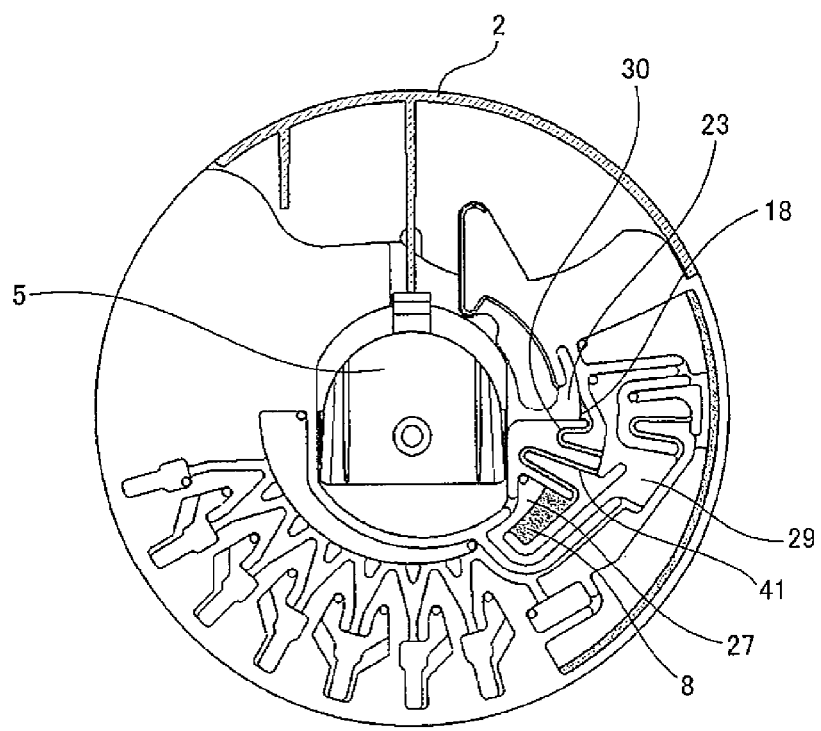
FIG. 14B is a sectional view showing that the sample liquid is sucked into a connecting passage 30 and the diluents is sucked into a connecting passage 41 by stopping a rotation.

Next, when the rotation of the rotor 101 is stopped, the sample liquid 18 is sucked into a connecting passage 30 as shown in FIG. 14B. The connecting passage 30 is siphon-shaped and connects the sample liquid receiving cavity 23 and the mixing cavity 29. The diluent 8 is similarly sucked into a connecting passage 41 that is siphon-shaped and connects the retaining cavity 27 and the mixing cavity 29.

Step 4

Figure 16A:
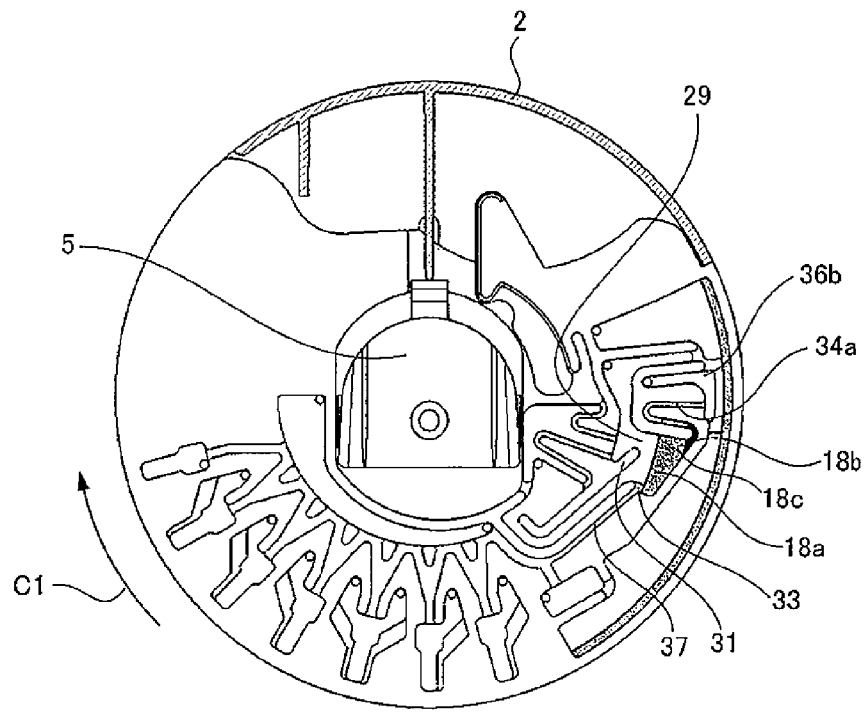
FIG. 16A is a sectional view showing the analyzing device of step 4.

When the rotor 101 is rotationally driven in a counterclockwise direction (direction C1), as shown in FIG. 16A, the sample liquid 18 in the sample liquid receiving cavity 23 and the diluent 8 in the retaining cavity 27 flow into the mixing cavity 29 and are centrifugally separated into a dilute plasma component 18a and a blood cell component 18b in the mixing cavity 29. Reference character 18c denotes a separation interface of the diluted plasma component 18a and the blood cell component 18b. The sample liquid 18 and the diluent 8 collide with the rib 31 once and then flow into the mixing cavity 29, so that the plasma component in the sample liquid 18 and the diluent 8 can be uniformly stirred.

Next, the absorbance of the diluted plasma component 18a is measured (secondary photometry) that has been centrifugally separated in the mixing cavity 29. To be specific, the analyzing device 1 is rotationally driven in the counterclockwise direction (direction C1) and the arithmetic unit 110 reads a detected value of the photodetector 113b when the mixing cavity 29 containing the diluted plasma component 18a passes between the light source 112b and the photodetector 113b.

In the present embodiment, blood serving as the sample liquid 18 and the diluent 8 are directly mixed and then the diluted plasma component 18a is extracted. Further, the diluted plasma component 18a is reacted with a reagent to analyze a specific component in the plasma component. The ratio of a plasma component in blood varies among individuals and thus the dilution factor of the plasma component greatly varies in direct mixing. Hence, in a reaction of the diluted plasma component 18a and the reagent, a reaction concentration varies and affects the measurement accuracy. In order to correct the variations in dilution factor at the mixing of the sample liquid 18 and the diluent 8, a diluent having a specified absorbance in a specific wave range is used, an absorbance is measured at the same point of the mixing cavity 29 before and after the mixing with the sample liquid, and a dilution factor is calculated. Thus it is possible to eliminate variations in the optical path length of a measured part, measure a dilution factor with high accuracy, and correct variations in dilution factor in the measurement results of the measurement cells, thereby remarkably improving the measurement accuracy. This correcting method is also useful for correcting variations in dilution factor when the variations are caused by varying quantities of the sample liquid 18 and the diluent 8.

Step 5

Figure 16B:
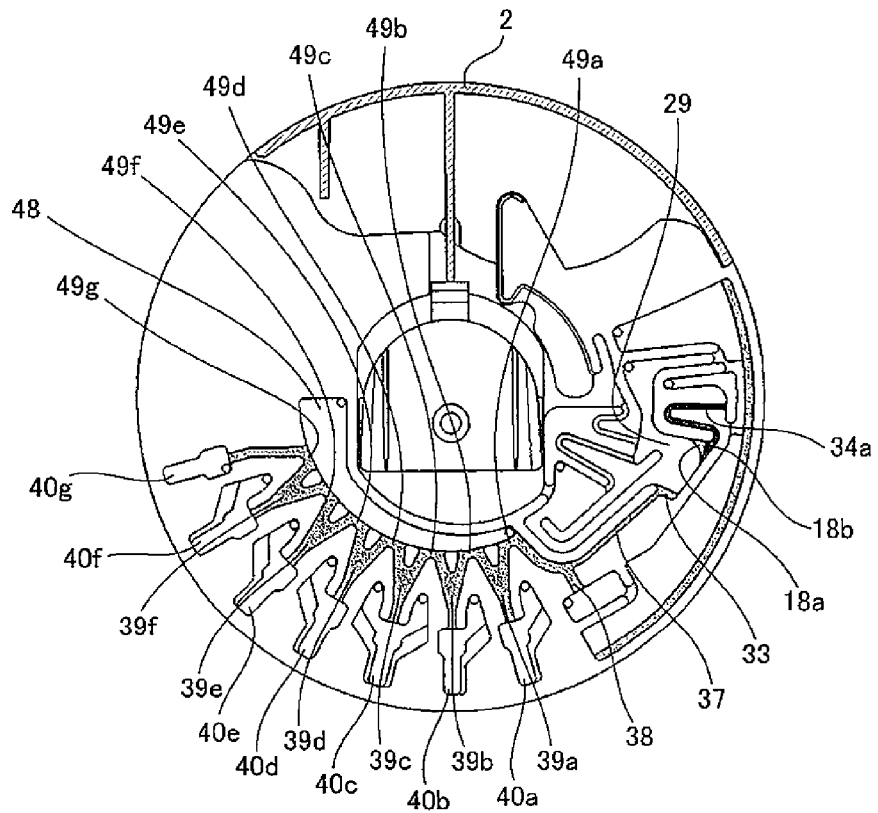
FIG. 16B is a sectional view showing the analyzing device of step 5.

Next, when the rotation of the rotor 101 is stopped, the diluted plasma component 18a is sucked by a capillary cavity 33 formed on the wall surface of the mixing cavity 29 and flows into, as shown in FIG. 16B, the overflow passage 38 and measuring passages 39a, 39b, 39c, 39d, 39e, 39f, and 39g through a capillary passage 37 communicating with the capillary cavity 33, and a fixed quantity of the diluted plasma component 18a is retained in each of the measuring passages 39a to 39g.

Figure 17A:
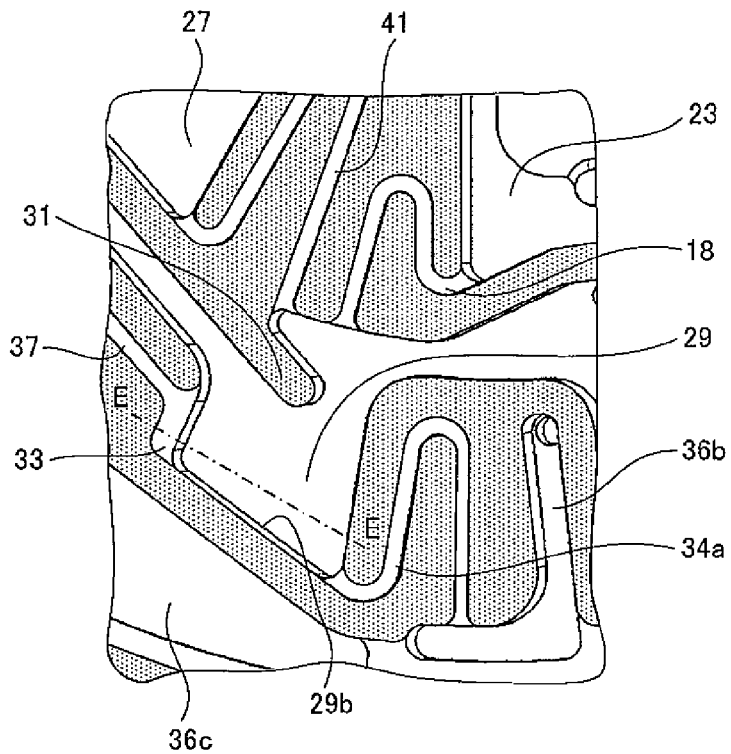
FIG. 17A is an enlarged perspective view showing a capillary cavity 33 and a portion around the capillary cavity 33.
Figure 17B:
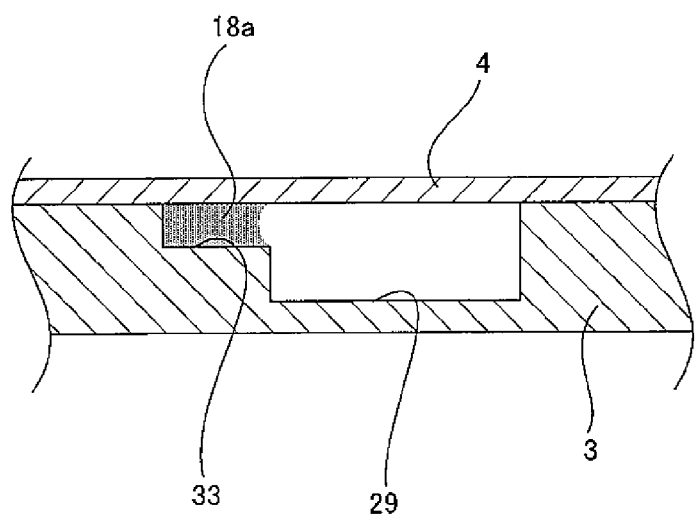
FIG. 17B is an E-E sectional view of step 5.

FIG. 17A is a perspective view showing the capillary cavity 33 and a portion around the capillary cavity 33. FIG. 17B is an E-E sectional view of FIG. 17A. The following will specifically describe the capillary cavity 33 and the portion around the capillary cavity 33.

The capillary cavity 33 is formed from a bottom 29b of the mixing cavity 29 to the inner periphery. In other words, the outermost position of the capillary cavity 33 is extended outside the separation interface 18c of the diluted plasma component 18a and the blood cell component 18b of FIG. 16A. By setting the position of the outer periphery of the capillary cavity 33 thus, the outer end of the capillary cavity 33 is immersed in the diluted plasma component 18a and the blood cell component 18b that have been separated in the mixing cavity 29. Since the diluted plasma component 18a has a lower viscosity than the blood cell component 18b, the diluted plasma component 18a is first sucked by the capillary cavity 33. The diluted plasma component 18a can be transferred to measurement cells 40a to 40f, and 40g through the capillary passage 37, the overflow passage 38, and the measuring passages 39a, 39b, 39c, 39d, 39e, 39f, and 39g.

After the diluted plasma component 18a is sucked, the blood cell component 18b is also sucked following the diluted plasma component 18a. Thus the diluted plasma component 18a can be replaced with the blood cell component 18b in the capillary cavity 33 and a path halfway to the capillary passage 37. When the overflow passage 38 and the measuring passages 39a to 39g are filled with the diluted plasma component 18a, the transfer of the liquid is stopped also in the capillary passage 37 and the capillary cavity 33, so that the blood cell component 18b does not enter the overflow passage 38 and the measuring passages 39a to 39g.

Hence, it is possible to minimize a loss of the transferred liquid as compared with the configuration of the prior art, thereby reducing a quantity of the sample liquid required for measurement.

Step 6

Figure 18A:
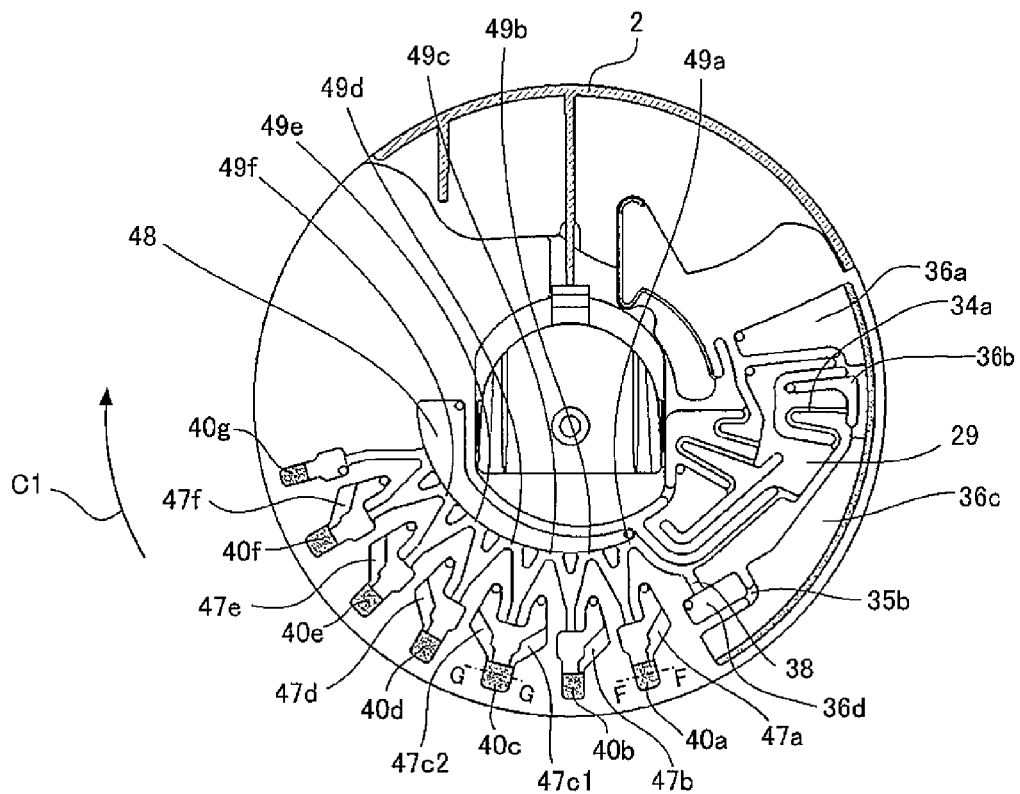
FIG. 18A is a sectional view showing the analyzing device of step 6.

Further, when the rotor 101 is rotationally driven in the counterclockwise direction (direction C1), as shown in FIG. 18A, the diluted plasma component 18a retained in the measuring passages 39a to 39g overflows at the positions of bending portions 49a, 49b, 49c, 49d, 49e, 49f, and 49g that are connected to the an atmosphere open cavity 48 communicating with the atmosphere, and then the diluted plasma component 18a flows into the measurement cells 40a to 40f, and 40g. At this point, equal quantities of the diluted plasma component 18a flow into the respective measurement cells 40a to 40f.

Moreover, the diluted plasma component 18a of the overflow passage 38 at this point flows into the overflow cavities 36c and 36a through the overflow cavity 36d and the backflow preventing passage 35b. Further, the sample liquid in the mixing cavity 29 at this point flows into the overflow cavities 36a and 36c through the siphon-shaped connecting passage 34a and the overflow cavity 36b.

The measurement cells 40a to 40f and 40g are extended in a direction along which a centrifugal force is applied. To be specific, the measurement cells are extended from the rotation center of the analyzing device 1 to the outermost periphery and have small widths in the circumferential direction of the analyzing device 1. The bottoms of the outer peripheries of the multiple measurement cells 40a to 40f and 40g are arranged at the same radius of the analyzing device 1. Thus for the measurements of the multiple measurement cells 40a to 40f and 40g, it is not necessary to provide the multiple light sources 112a of the same wavelength and the multiple photodetectors 113a at different radius distances corresponding to the light sources 112a, thereby reducing the cost of the apparatus. Since measurements can be conducted using different wavelengths in the same measurement cell, the sensitivity of measurement can be improved by selecting the optimum wavelength according to the concentration of a mixed solution.

Figure 20A:
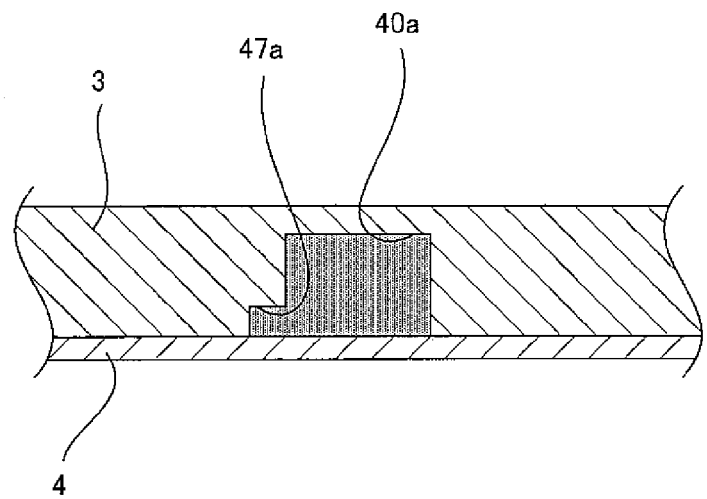
FIG. 20A is an F-F sectional view of FIG. 18A.

On one side walls of the side walls of the measurement cells 40a, 40b, and 40d to 40f, the side walls being arranged in the circumferential direction, capillary areas 47a, 47b, 47d, 47e, and 47f are formed so as to extend from the outer periphery positions to the inner peripheries of the measurement cells. FIG. 20A is an F-F sectional view of FIG. 18A.

Figure 20B:
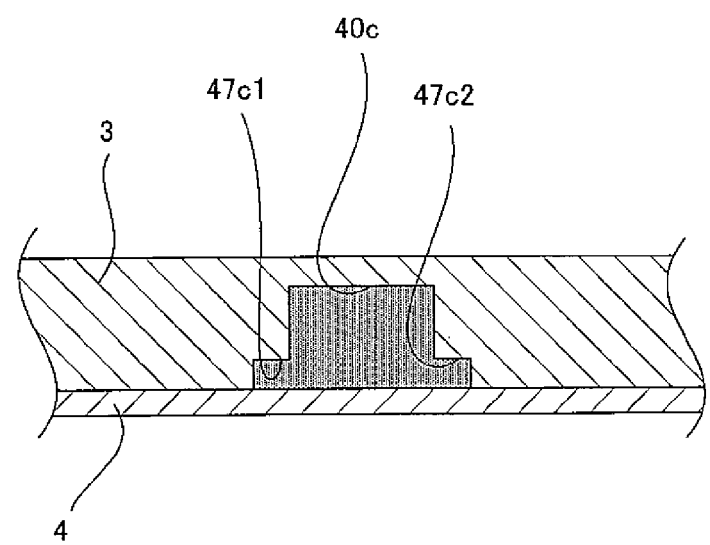
FIG. 20B is a G-G sectional view of FIG. 18A.

On both side walls of the measurement cell 40c in the circumferential direction, capillary areas 47c1 and 47c2 are formed so as to extend from the outer periphery position to the inner periphery of the measurement cell. FIG. 20B is a G-G sectional view of FIG. 18A.

Unlike in the measurement cells 40a to 40f, a capillary area is not formed in the measurement cell 40g.

The suction capacity of the capillary area 47a is not so large as to fully accommodate the sample liquid retained in the measurement cell 40a. Similarly, the capacities of the capillary areas 47b and 47d to 47f are not so large as to fully accommodate the sample liquid retained in the measurement cells 40b and 40d to 40f. As to the capillary areas 47c1 and 47c2 of the measurement cell 40c, the sum of the suction capacities of the capillary area 47c1 and the capillary area 47c2 is large enough to fully accommodate the sample liquid retained in the measurement cell 40c. The measurement cells 40b to 40f and 40g have equal optical path lengths.

Figure 19:
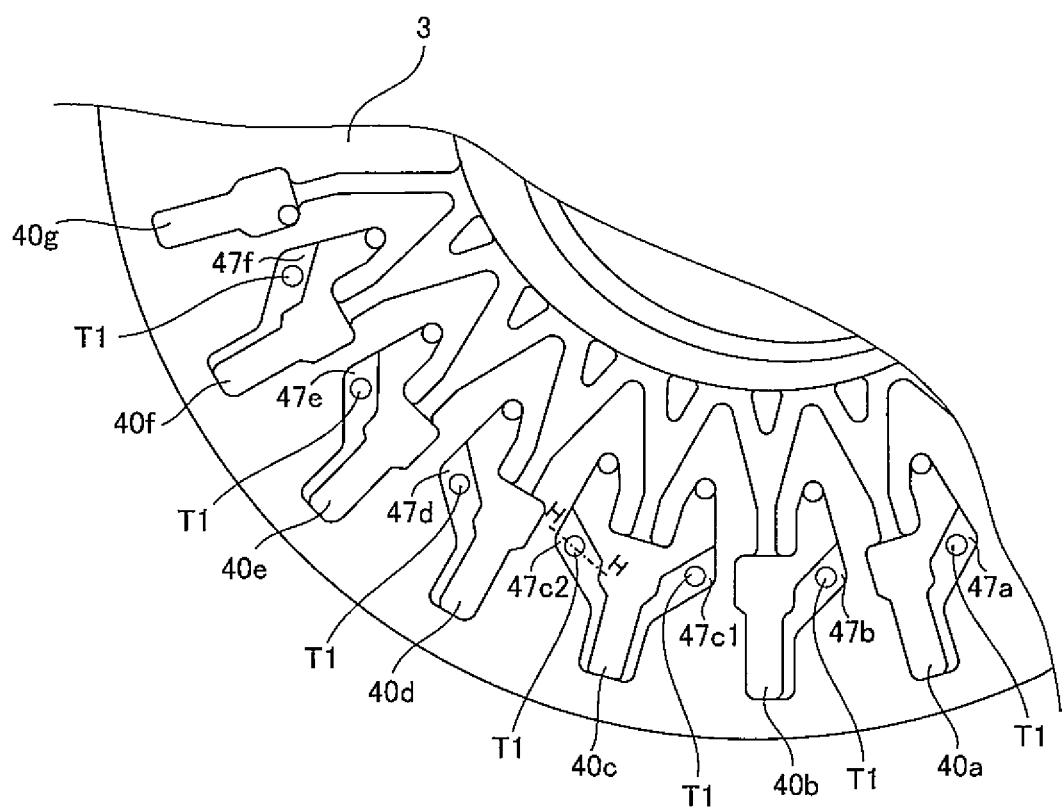
FIG. 19 is an enlarge plan view showing measurement cells 40a to 40f of FIG. 12.

As shown in FIG. 19, the capillary areas 47a, 47b, 47c1, 47c2, 47d, 47e, and 47f each contain a reagent T1 to be reacted with the sample liquid. The measurement cell 40g does not contain any reagents. The reagent T1 contained in the capillary areas 47a, 47b, 47c1, 47c2, and 47d to 47f varies according to a specific component to be analyzed. Soluble reagents are contained in the capillary areas 47a, 47b, and 47d to 47f and less soluble reagents are contained in the capillary areas 47c1 and 47c2.

Figure 23A:
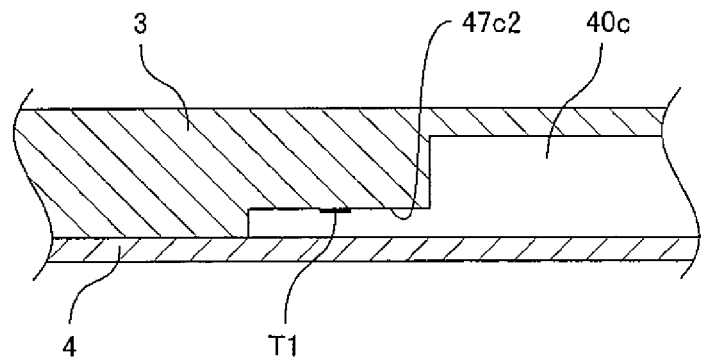
FIG. 23A is an enlarged sectional view of the analyzing device taken along line H-H of FIG. 9.

FIG. 23A is an enlarged view showing a part of the capillary area 47c2 of the analyzing device 1 that is cut along line H—H. The reagent T1 is disposed on the plane of the capillary area 47c2 formed in the base substrate 3. The other capillary areas 47a, 47b, 47c1, and 47d to 47f are configured like the capillary area 47c2.

Step 7

Figure 18B:
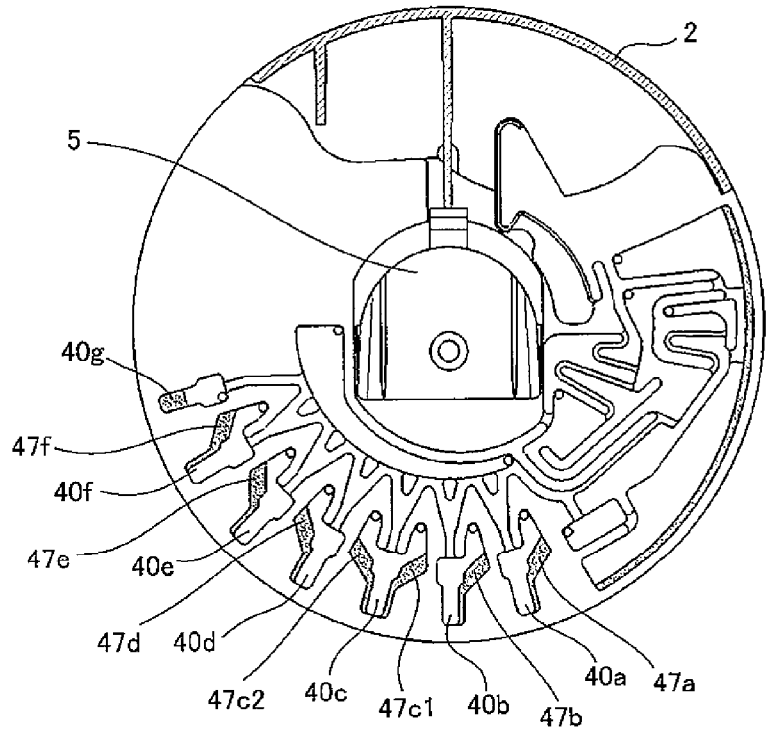
FIG. 18B is a sectional view showing the analyzing device of step 7.

Next, the rotation of the analyzing device 1 is slowed or stopped or the analyzing device 1 is vibrated so as to laterally reciprocate at the predetermined stop position with respect to the rotation axis 107 with the predetermined amplitude range and the predetermined period, so that the sample liquid transferred to the measurement cells 40a to 40f or a mixed solution of the reagent and the sample liquid is sucked into the capillary areas 47a to 47f by a capillary force as shown in FIG. 18B. At this point, the dissolution of the reagent T1 is started and a reaction of the specific component contained in the diluted plasma component 18a and the reagent is started.

Step 8

As shown in FIG. 18B, from a state in which the sample liquid or the mixed solution of the reagent and the sample liquid is sucked to the capillary areas 47a to 47f, the rotation of the analyzing device 1 is accelerated and the analyzing device 1 is rotationally driven in the counterclockwise direction (direction C1) or the clockwise direction (direction C2). Thus as shown in FIG. 18A, the liquid retained in the capillary areas 47a to 47f is transferred to the outer peripheries of the measurement cells 40a to 40f by a centrifugal force, so that the reagent T1 and the diluted plasma component 18a are agitated.

In this case, the repeated operations of step 7 and step 8 accelerate the agitation of the reagent and the diluted plasma component 18a. Thus it is possible to reliably agitate the reagent and the diluted plasma component 18a in a short time as compared with agitation only by diffusion.

Step 9

When the analyzing device 1 is rotationally driven in the counterclockwise direction (direction C1) or the clockwise direction (direction C2) and the measurement cells 40a to 40f and 40g pass between the light source 112a and the photodetector 113a, the arithmetic unit 110 reads a detected value of the photodetector 113a and corrects the detected value according to the results of the primary photometry and the secondary photometry to calculate the concentration of a specific component.

The measurement result of the measurement cell 40g is used as the reference data of the measurement cells 40a to 40f during computations in the arithmetic unit 110.

In this way, the diluent container 5 can be opened by opening/closing the protective cap 2 when a user collects a sample liquid, so that the diluent can be transferred into the analyzing device 1. Thus it is possible to simplify the analyzing apparatus, reduce the cost, and improve operability for the user.

Further, the diluent container 5 is used that is sealed with the aluminum seal 9 serving as a sealing member and the diluent container 5 is opened by breaking the aluminum seal 9 with the opening rib 14 serving as a projecting portion. Thus the diluent does not evaporate or decrease in quantity during long-term storage, thereby improving the accuracy of analysis.

In a state of shipment of the analyzing device 1 shown in FIG. 6(a), the latch portion 10 of the diluent container 5 is engaged with the locking groove 12 of the closed protective cap 2, and the diluent container 5 is locked at the liquid retaining position so as not to move in the direction of arrow J. Although the diluent container 5 can be moved in the diluent container storage part 11 by the opening and closing operations of the protective cap 2, the diluent container 5 is not erroneously opened or the diluent does not leak during transportation by the user before use. This is because the position of the diluent container 5 in the diluent container storage part 11 is locked at the liquid retaining position in a period before the user opens the protective cap 2 to use the analyzing device 1.

The widths of the measurement cells 40a to 40f and 40g (dimensions in the circumferential direction) formed to extend in the centrifugal direction (radial direction) of the analyzing device 1 are regulated to the minimum dimensions detectable by the optical measurement unit 108, and the levels of liquids retained in the measurement cells 40a to 40f and 40g during rotation are regulated to radial positions detectable by the optical measurement unit 108, that is, liquid levels filling light irradiation areas, so that a measurement can be conducted with the minimum liquid volume.

As previously mentioned, steps 7 to 9 are performed in a state in which the measurement cells 40a to 40f are formed to extend in the direction along which a centrifugal force is applied and the capillary areas 47a to 47f are formed on the at least one side walls of the side walls arranged in the rotational direction so as to extend from the outer periphery positions to the inner peripheries of the measurement cells 40a to 40f. Thus it is possible to obtain a sufficient agitating effect and reduce the size of the analyzing device without providing a U-shaped agitating mechanism of patent document 1 in which the agitating mechanism for agitating a sample liquid and a reagent is made up of the inlet passage 114, the measurement cell 115, and the passage 117.

The measurement cells 40a to 40f and 40g are formed to extend in the direction along which a centrifugal force is applied. Thus the quantity of sample liquid filling the measurement cells is smaller than that of patent document 1 and a measurement can be conducted with a small quantity of sample liquid.

Figure 21:
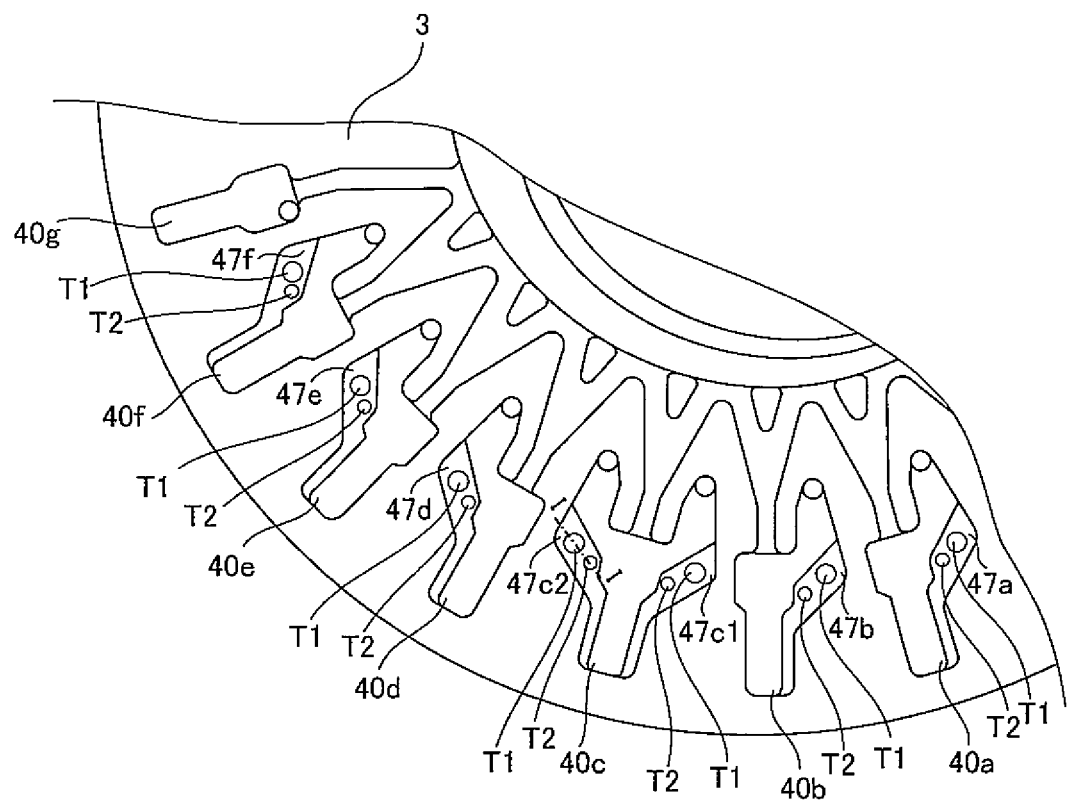
FIG. 21 is an enlarged plan view showing another example of the measurement cells 40a to 40f.

In the present embodiment, the reagent T1 is retained in the capillary areas 47a to 47f. As shown in FIG. 21, the capillary areas 47a to 47f may contain the reagent T1 and a reagent T2 that is different from the reagent T1.

Figure 24A:
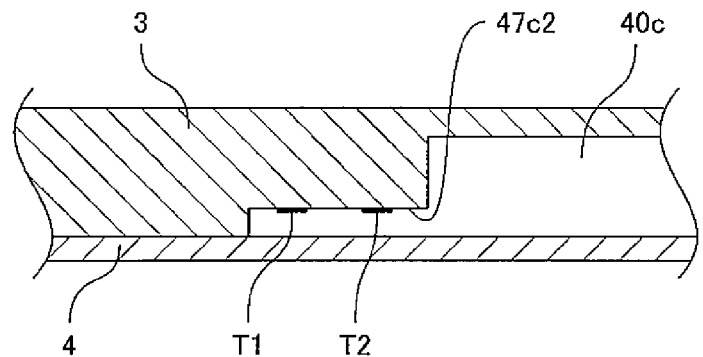
FIG. 24A is an enlarged sectional view taken along line I-I of FIG. 21.

FIG. 24A is an enlarged view showing a part of the capillary area 47c2 of the analyzing device 1 that is cut along line I-I. The reagents T1 and T2 are disposed on the plane of the capillary area 47c2 formed in the base substrate 3. The other capillary areas 47a, 47b, 47c1, and 47d to 47f are configured like the capillary area 47c2.

Figure 22:
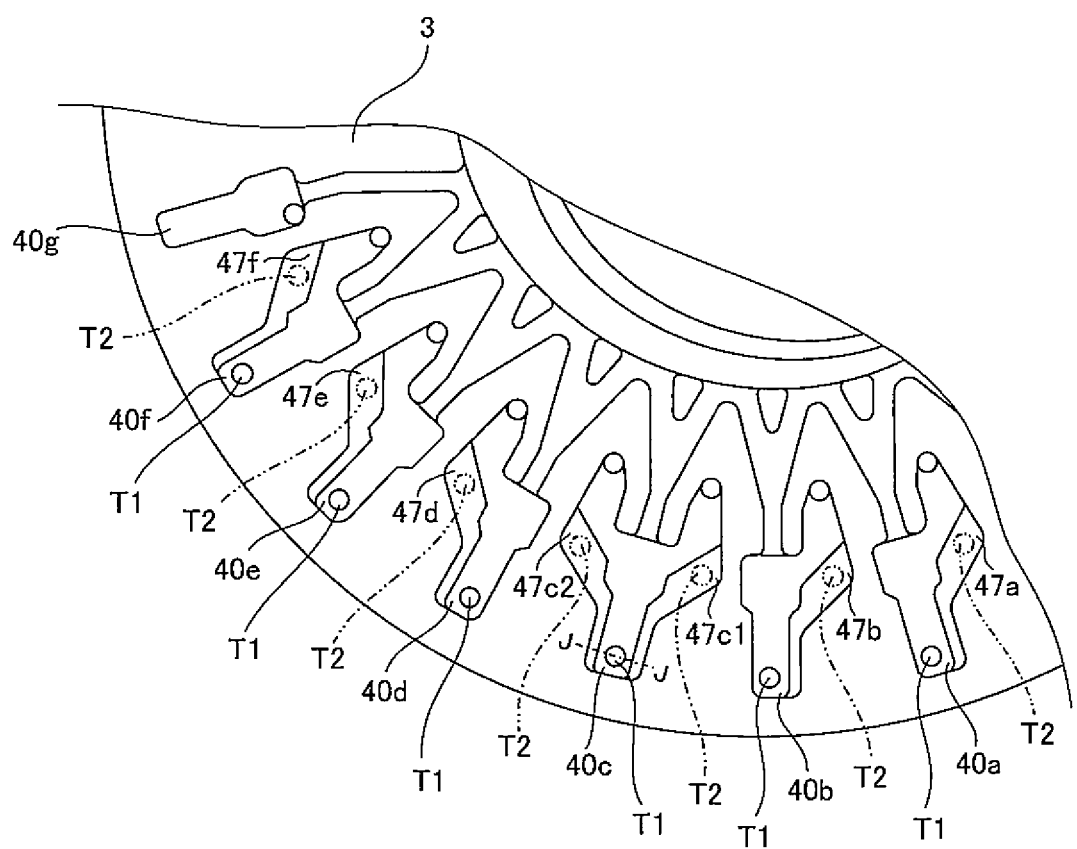
FIG. 22 is an enlarged plan view showing still another example of the measurement cells 40a to 40f.

As shown in FIG. 22, the reagent T1 may be provided around the bottoms of the outer peripheries of the measurement cells 40a to 40f and the reagent T2 may be contained in the capillary areas 47a, 47b, 47c1, 47c2, and 47d to 47f when necessary as indicated by virtual lines. When the reagent T1 is provided on the bottom of one of the measurement cells and the reagent T2 is provided in the capillary area of the measurement cell, the reagent T1 and the reagent T2 may contain the same component or different components. The reagent T2 provided in the capillary areas may be multiple reagents of different components.

Figure 25A:
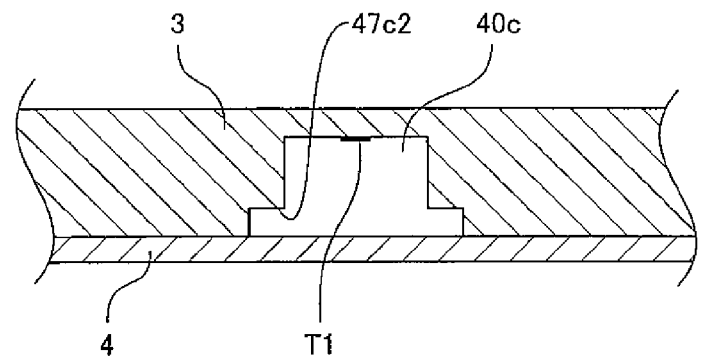
FIG. 25A is an enlarged sectional view taken along line J-J of FIG. 22.

FIG. 25A is an enlarged view showing a part of the measurement cell 40c of the analyzing device 1 that is cut along line J-J. The reagent T1 is disposed on the plane of the measurement cell 40c. The other measurement cells 40a, 40b, 47c1, and 47d to 47f are configured like the measurement cell 40c.

Figure 23B:
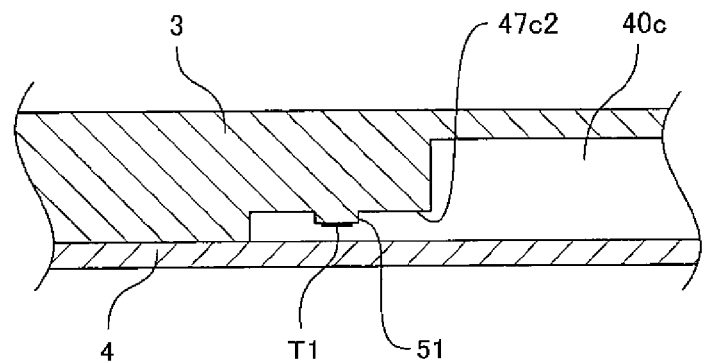
FIG. 23B is an H-H enlarged sectional view showing another specific example.
Figure 24B:
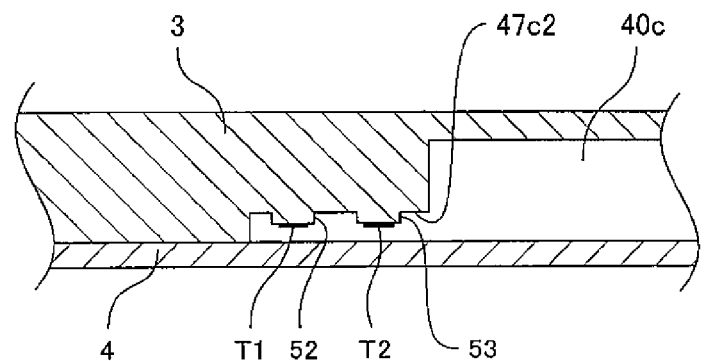
FIG. 24B is an I-I enlarged sectional view showing another specific example.
Figure 25B:
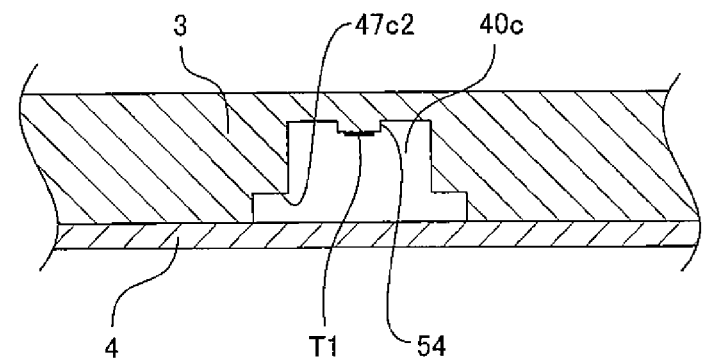
FIG. 25B is a J-J enlarged sectional view showing another specific example.

FIGS. 23B, 24B, and 25B show other examples in which the analyzing device 1 is cut on the same part as in FIGS. 23A, 24A, and 25A.

FIG. 23B will be described below.

In FIG. 23A, the reagent T1 is applied on the plane of the capillary area 47c2, whereas in the specific example of FIG.

23B, the reagent T1 is disposed on a projecting portion 51 that is formed with a height of several tens μm on the plane of the capillary area 47c2.

FIG. 24B will be described below.

In FIG. 24A, the reagents T1 and T2 are applied on the plane of the capillary area 47c2, whereas in the specific example of FIG. 24B, the reagent T1 is disposed on a projecting portion 52 formed with a height of several tens μm on the plane of the capillary area 47c2, and the reagent T2 is disposed on a projecting portion 53 formed with a height of several tens μm on the plane of the capillary area 47c2. In FIG. 24A, since the applied reagents spread on the plane of the capillary area 47c2, the adjacent reagents have to be spaced apart, whereas the reagents T1 and T2 applied on the projecting portions 52 and 53 are not spaced apart but do not come into contact with each other, which is effective at reducing the size of the analyzing device 1. Further, a capillary force increases because of a small spacing between the projecting portions 52 and 53 and the cover substrate 4. Thus the sample liquid inevitably flows in contact with the reagents T1 and T2, so that the reagents are sufficiently dissolved and higher measurement accuracy can be expected.

The following will describe FIG. 25B.

In FIG. 25A, the reagent T1 is applied on the plane of the measurement cell 40, whereas in the specific example of FIG. 25B, the reagent T1 is disposed on a projecting portion 54 formed with a height of several tens μm on the plane of the measurement cell 40.

In the analyzing methods of the foregoing embodiment, in steps 1 to 6, the analyzing device 1 is rotated and the sample liquid is transferred to the measurement cells 40a to 40f by a generated centrifugal force. In steps 7 and 8, the rotation of the analyzing device 1 is slowed or stopped to suck the sample liquid of the measurement cells to the capillary areas 47a to 47f by a capillary force, and then the rotation of the analyzing device 1 is accelerated such that the sample liquid is returned to the outermost parts of the measurement cells 40a to 40f and is agitated therein after the sample liquid sucked in the capillary areas 47a to 47f reacts with the dissolved reagents. At this point, light passing through the sample liquid in the measurement cells 40a to 40f is detected and a component is analyzed relative to a reference that is the detected value of light passing through the sample liquid in the measurement cell 40g. By implementing the following analyzing method, it is possible to eliminate the need for the measurement cell 40g for reference measurement, thereby reducing the size of the analyzing device 1.

To be specific, the sample liquid is supplied to the outermost parts of the measurement cells 40a to 40f by rotating the analyzing device and the detected value of light passing through the sample liquid is detected as a reference before the sample liquid reacts with the reagent. Further, the centrifugal force applied to the sample liquid is reduced from that of reference measurement to suck the sample liquid into the capillary areas 47a to 47f, the reagent is dissolved with the sample liquid, the centrifugal force is applied to the dissolved reagent in the capillary areas 47a to 47f to move the reagent and the reacted sample liquid to the outermost parts of the measurement cells 40a to 40f, the detected value of light passing through the sample liquid is measured, and then the detected value is compared with the reference to analyze a component of the sample liquid.

In this way, the detected value of light passing through the reagent and the reacted sample liquid is evaluated in each of the measurement cells 40a to 40f, so that higher measurement accuracy can be expected.

Second Embodiment

FIGS. 26A, 26B to 28A, 28B, and 28C show a second embodiment of the present invention.

In the first embodiment, the capillary areas 47a, 47b, 47c1, 47c2, and 47d to 47f formed so as to extend from the outer periphery positions to the inner peripheries of the measurement cells 40a to 40f have one sides in contact with the side walls of the respective measurement cells. The second embodiment is different from the first embodiment only in the following configuration.

Figure 26A:
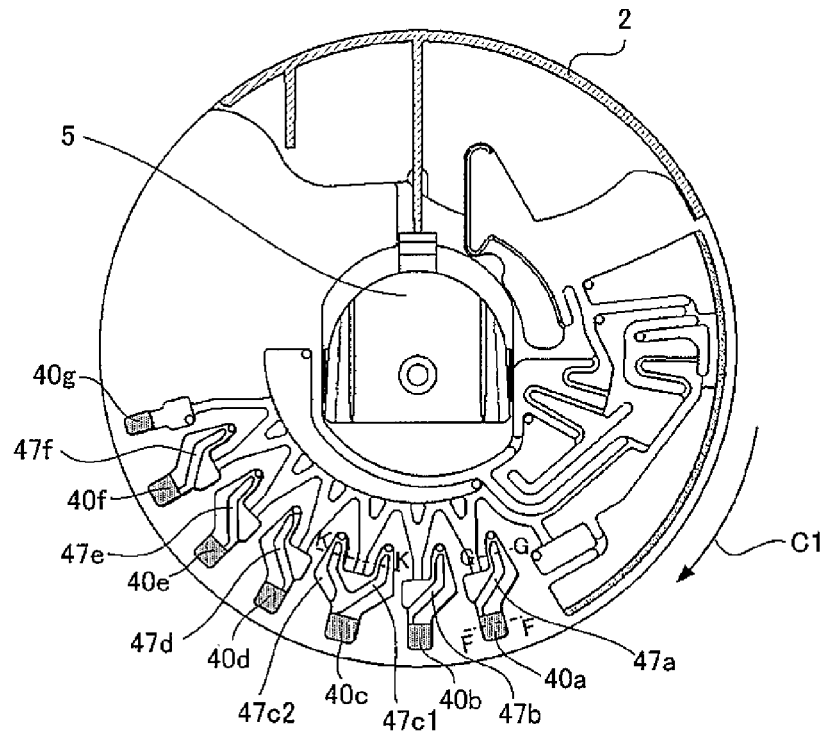
FIG. 26A is a sectional view showing step 6 according to a second embodiment of the present invention.

FIG. 26A shows step 6 in which a rotor 101 is rotationally driven in a counterclockwise direction (direction C1), so that a diluted plasma component 18a retained in measuring passages 39a to 39g overflows at the positions of bending portions 49a, 49b, 49c, 49d, 49e, 49f, and 49g, and then the diluted plasma component 18a flows into measurement cells 40a to 40f, and 40g.

The measurement cells 40a to 40f and 40g are formed so as to extend in a direction along which a centrifugal force is applied. To be specific, the measurement cells are extended from the rotation center of an analyzing device 1 to the outermost periphery and have small widths in the circumferential direction of the analyzing device 1. The bottoms of the outer peripheries of the multiple measurement cells 40a to 40f and 40g are arranged at the same radius of the analyzing device 1. Thus for the measurements of the multiple measurement cells 40a to 40f and 40g, it is not necessary to provide multiple light sources 112a of the same wavelength and multiple photodetectors 113a at different radius distances corresponding to the light sources 112a, thereby reducing the cost of the apparatus. Since measurements can be conducted using different wavelengths in the same measurement cell, the sensitivity of measurement can be improved by selecting the optimum wavelength according to the concentration of a mixed solution.

Figure 27:
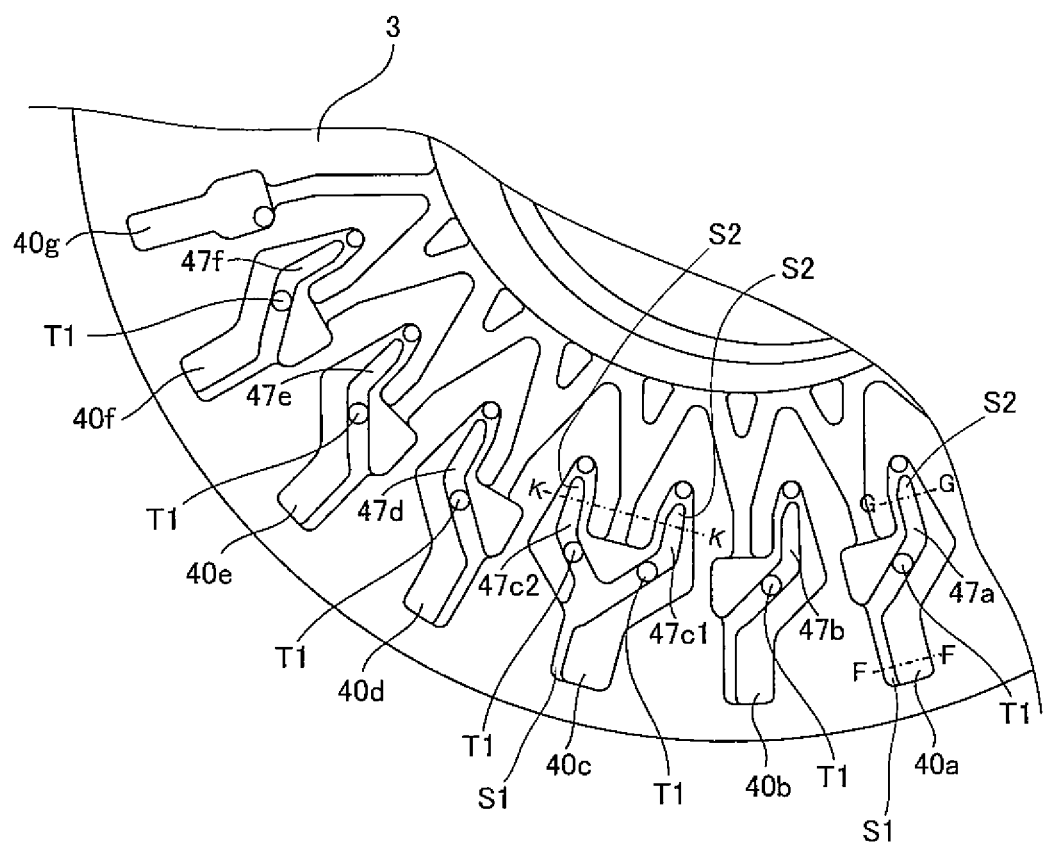
FIG. 27 is an enlarged plan view showing measurement cells 40a to 40f of FIG. 26.
Figure 28A:
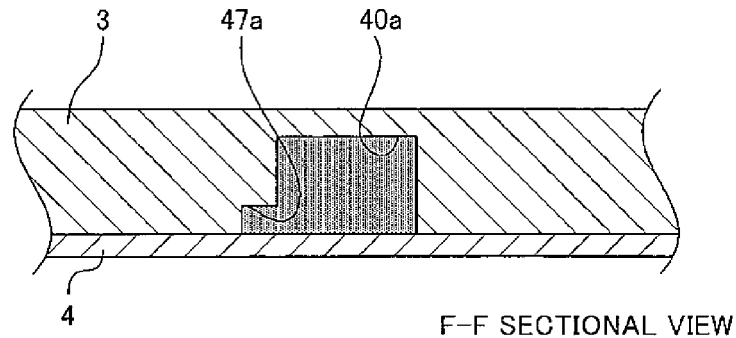
FIG. 28A is an F-F sectional view of FIG. 27.
Figure 28B:
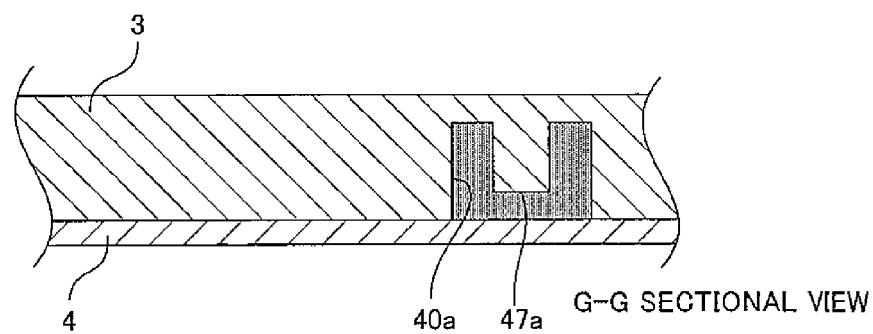
FIG. 28B is a G-G sectional view of FIG. 27.

In the second embodiment, as shown in FIG. 27, capillary areas 47a, 47b, 47c1, 47c2, and 47d to 47f are extended from the outer periphery positions to the inner peripheries of the measurement cells. Further, the capillary areas 47a to 47f have one ends S1 connected to one side walls of the measurement cells 40a to 40f, the side walls being arranged in a rotational direction. Moreover, the capillary areas 47a to 47f have one ends S2 formed at the inner periphery positions such that the one ends S2 are separated from the side walls of the measurement cells 40a to 40f, the side walls being arranged in the rotational direction. FIG. 28A is an F-F sectional view of FIG. 27. FIG. 28B is a G-G sectional view of FIG. 27. The one ends S1 of the capillary areas 47b to 47f are formed as on the capillary area 47a.

Figure 28C:
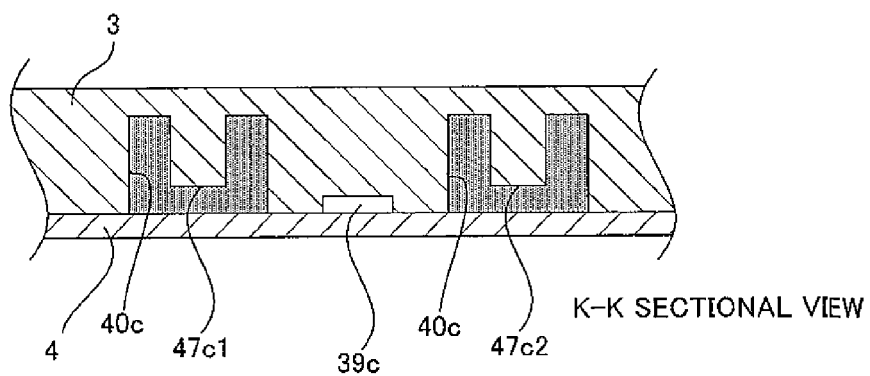
FIG. 28C is a K-K sectional view of FIG. 27.

The capillary area 47c provided in the measurement cell 40c has the one end S2 divided into two on the inner periphery position. The divided ends S2 are both separated from the side walls of the measurement cells 40a to 40f, the side walls being arranged in the rotational direction. FIG. 28C is a K-K sectional view of FIG. 27.

The second embodiment is similar to the first embodiment in that the measurement cell 40g does not have any capillary areas unlike the measurement cells 40a to 40f, a spacing between the capillary areas 47a to 47f, and 47g and a cover substrate 4 is 200 μm to 300 μm, and hydrophilic treatment is performed on a surface of the cover substrate 4 on the opposite side from the capillary areas 47a to 47f, and 47g.

The suction capacity of the capillary area 47a is not so large as to fully accommodate the diluted plasma component 18a that acts as a sample liquid retained in the measurement cell 40a. Similarly, the capacities of the capillary areas 47b and 47d to 47f are not so large as to fully accommodate the sample liquid retained in the measurement cells 40b and 40d to 40f. As to the capillary areas 47c1 and 47c2 of the measurement cell 40c, the sum of the suction capacities of the capillary area 47c1 and the capillary area 47c2 is large enough to fully accommodate the sample liquid retained in the measurement cell 40c.

As shown in FIG. 27, the capillary areas 47a, 47b, 47c1, 47c2, 47d, 47e, and 47f each contain a reagent T1 to be reacted with the sample liquid. The measurement cell 40g does not contain any reagents. The reagent T1 contained in the capillary areas 47a, 47b, 47c1, 47c2, and 47d to 47f varies according to a specific component to be analyzed. Soluble reagents are contained in the capillary areas 47a, 47b, and 47d to 47f and a less soluble reagent is contained in the capillary area 47c.

Figure 26B:
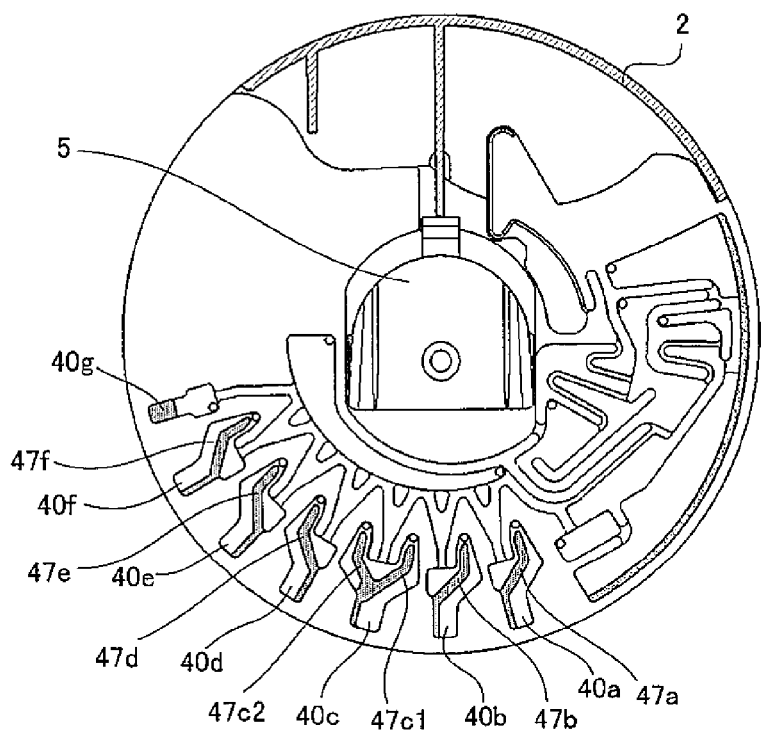
FIG. 26B is a sectional view showing step 7 according to the second embodiment.

In step 7 of the second embodiment, the rotation of the analyzing device 1 is vibrated so as to laterally reciprocate at a predetermined stop position with respect to a rotation axis 107 with a predetermined amplitude range and a predetermined period, so that as shown in FIG. 26B, the sample liquid transferred to the measurement cells 40a to 40f or a mixed solution of the reagent and the sample liquid is sucked to the capillary areas 47a to 47f by a capillary force. At this point, the dissolution of the reagent T1 is started and then a reaction of the specific component contained in the diluted plasma component 18a and the reagent is started.

When the mixed solution is sucked to the capillary areas 47a to 47f, only by slowing or stopping the rotation of the analyzing device 1, the mixed solution is sucked to the one ends S1 connected to the side walls of the measurement cells 40a to 40f in the rotational direction but the mixed solution may not be sucked to the one ends S2 separated from the side walls of the measurement cells 40a to 40f, the side walls being arranged in the rotational direction. Since the one ends S2 on the inner periphery positions of the capillary areas 47a to 47f are separated from the side walls of the measurement cells 40a to 40f in the rotational direction, the mixed solution was reliably sucked to the one ends S2 of the capillary areas 47a to 47f by a capillary force.

Figure 40A:
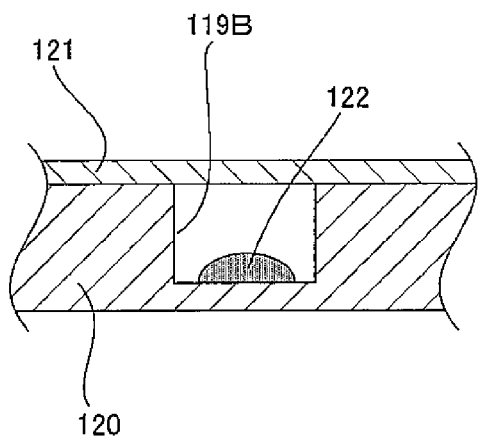
FIG. 40A is a sectional view showing a state in which a reagent 122 is dropped into a reaction chamber 119B of patent document 2.
Figure 40B:
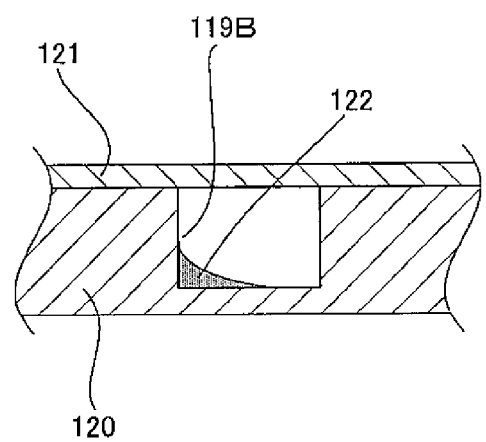
FIG. 40B is a sectional view showing a state after the reagent 122 is dropped into the reaction chamber 119B of patent document 2.
Figure 41:
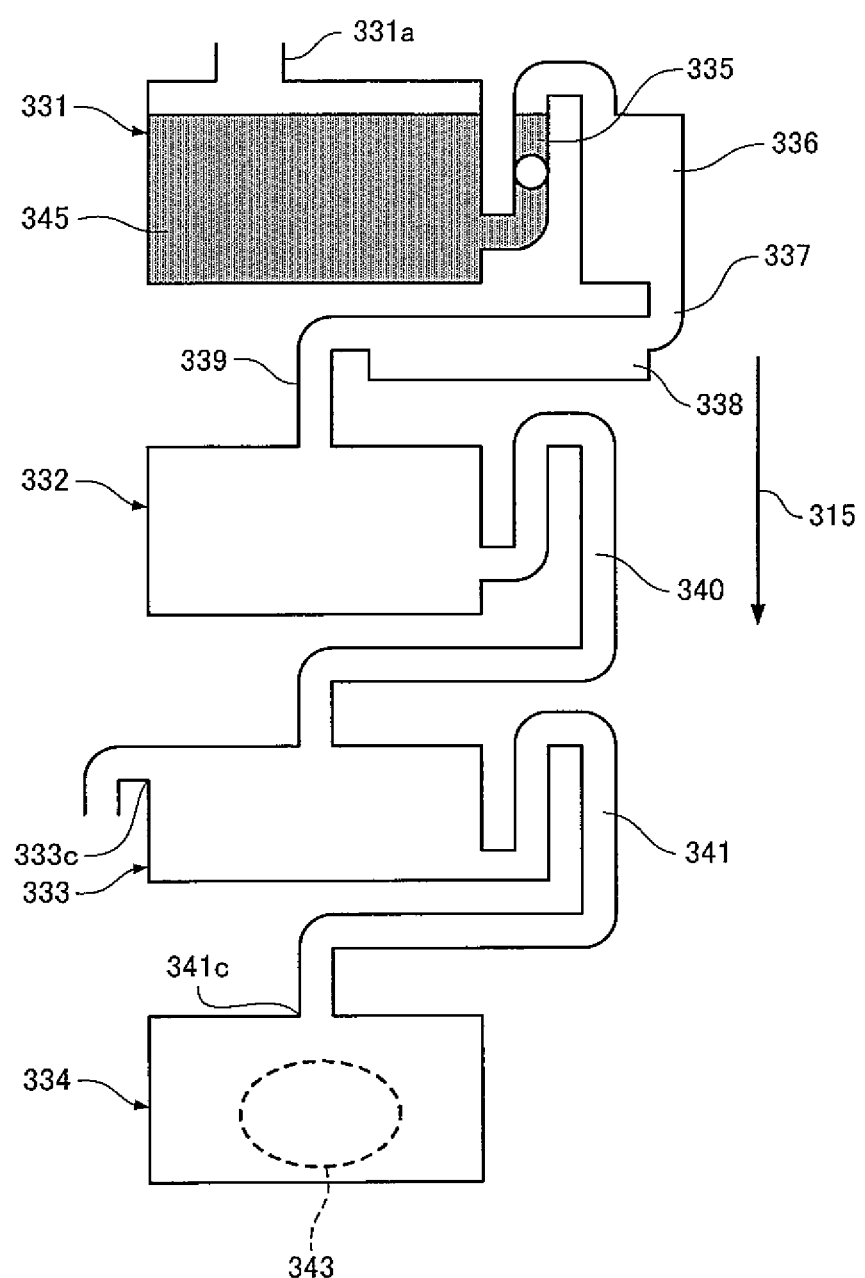
FIG. 41 is a plan view showing an analyzing device of patent document 3.

The reagent T1 is set on the one ends S2 that are formed on the inner periphery positions so as to be separated from the side walls of the capillary areas 47a to 47f, the side walls being arranged in the rotational direction. Thus without fully expanding the areas of the measurement cells 40a to 40f relative to the quantity of dropped reagent, the concentration of the reagent does not vary in the passages unlike in the prior art shown in FIGS. 40A and 40B, the reagent T1 becomes easy to dissolve, and a uniform color reaction can be expected. Steps 8 and 9 are similar to those of the first embodiment. Consequently, even when a small quantity of sample liquid is applied, it is possible to reduce variations in measurement result and expect higher accuracy of analysis.

Third Embodiment

Figure 29:
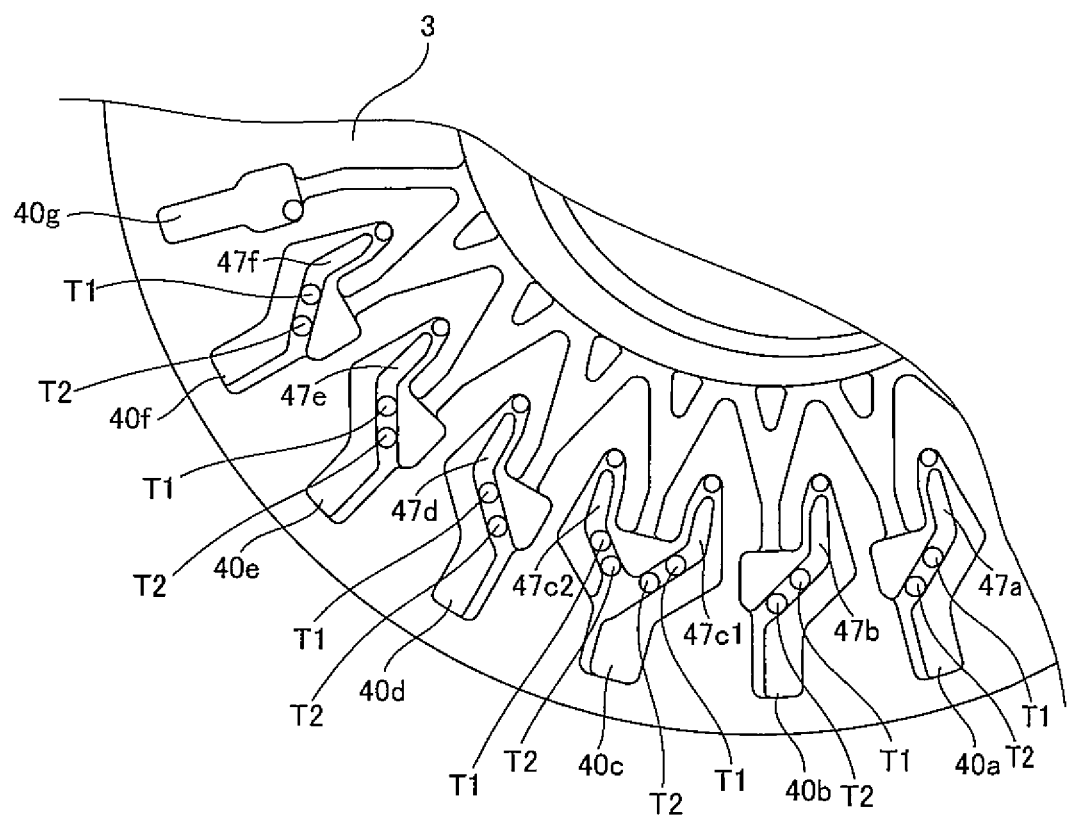
FIG. 29 is an enlarged plan view showing measurement cells 40a to 40f according to a third embodiment of the present invention.

FIG. 29 shows a third embodiment of the present invention.

In the second embodiment, the reagent T1 is contained in the capillary areas 47a to 47f. As shown in FIG. 29, multiple reagents T1 and T2 may be contained in capillary areas 47a to 47f.

When the capacities of the capillary areas 47a, 47b, and 47d to 47f are not so large as to fully accommodate a sample liquid retained in measurement cells 40a, 40b, and 40d to 40f, it is preferable to set less soluble one of the reagents outside the other reagent.

To be specific, in the case where the reagent T1 was a relatively soluble coloring matter that had a viscosity of 1.10 mPa·s and the reagent T2 was protein that had a viscosity of 3.02 mPa·s and was less soluble than the reagent T1, even when the capacities of the capillary areas 47a, 47b, and 47d to 47f were not so large as to fully accommodate the sample liquid retained in the measurement cells 40a, 40b, and 40d to 40f, it was confirmed that the reagents T1 and T2 were sufficiently dissolved through the agitation and mixing by setting the less soluble reagent T2 outside the soluble reagent T1. In a reversed arrangement where the reagent T1 was protein having a viscosity of 3.02 mPa·s and the reagent T2 was a coloring matter having a viscosity of 1.10 mPa·s, the reagent having a lower viscosity flowed to the outer periphery and interfered with the agitation and mixing, the quantities of liquid sucked into the capillary areas decreased, and only a supernatant part not containing the reagent having a lower viscosity in the sample liquid was sucked, resulting in low agitating effect. Thus the protein in the reagent T1 was not dissolved.

The specific example of the third embodiment described the case where the capacities of the capillary areas 47a, 47b, and 47d to 47f each of which contain the multiple reagents are not so large as to fully accommodate the sample liquid retained in the measurement cells 40a, 40b, and 40d to 40f. When the multiple reagents are disposed in the single capillary area, the reagent having a higher viscosity is set outside the other reagent. This configuration is effective also when the capacities of the capillary areas 47a, 47b, and 47d to 47f are large enough to fully accommodate the sample liquid retained in the measurement cells 40a, 40b, and 40d to 40f.

Fourth Embodiment

FIGS. 30 and 31A to 31E show a fourth embodiment of the present invention.

Figure 30:
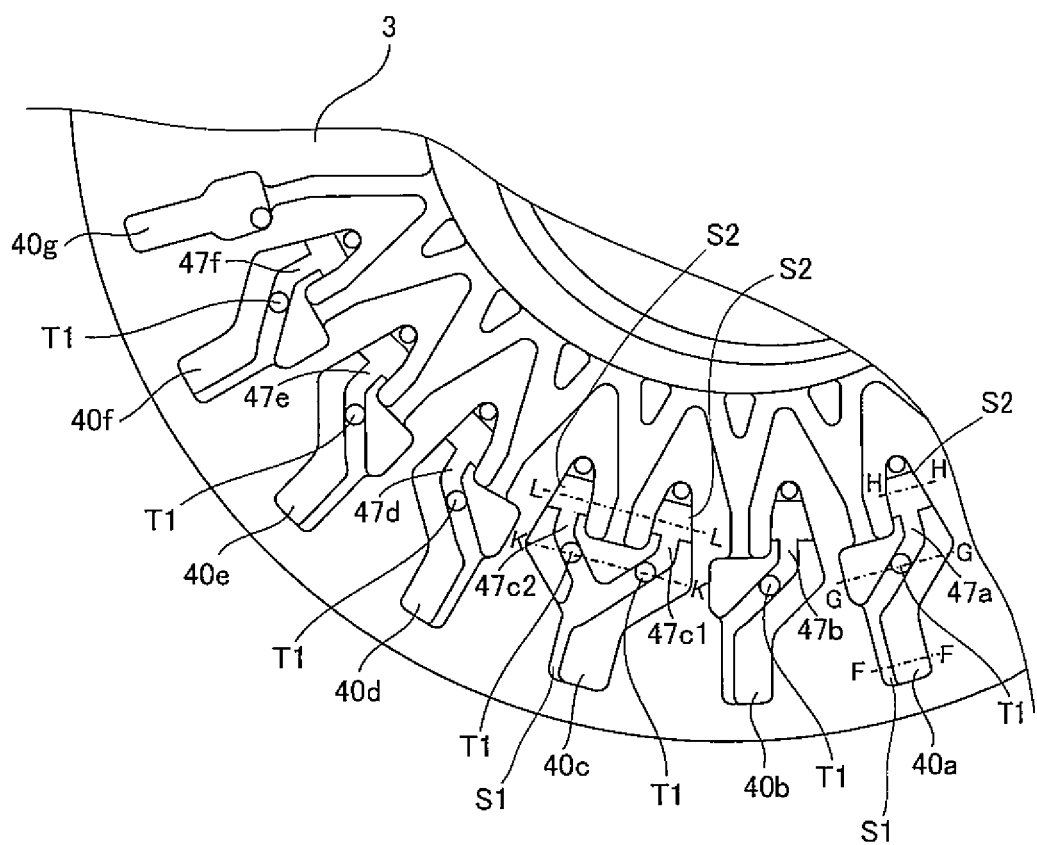
FIG. 30 is an enlarged plan view showing measurement cells 40a to 40f according to a fourth embodiment of the present invention.
Figure 31A:
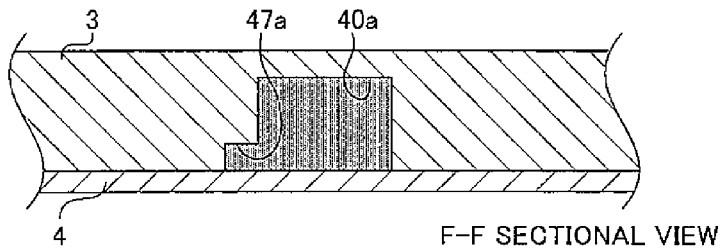
FIG. 31A is an F-F sectional view of FIG. 30.
Figure 31B:
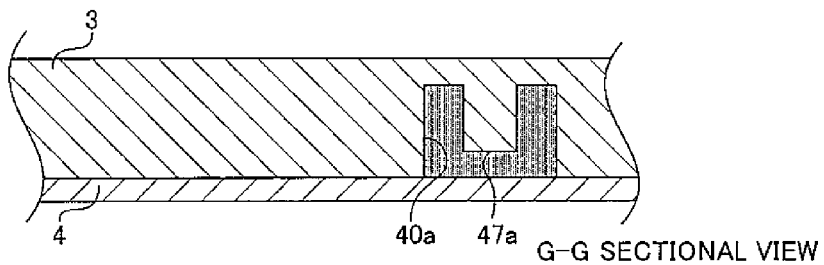
FIG. 31B is a G-G sectional view of FIG. 30.
Figure 31C:
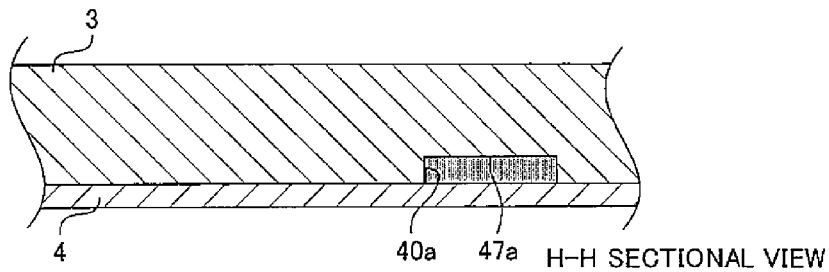
FIG. 31C is an H-H sectional view of FIG. 30.

In the second embodiment, as shown in FIG. 27, the one ends S2 of the capillary areas 47a to 47f provided in the measurement cells 40a to 40f are fully separated from the side walls of the measurement cells 40a to 40f, the side walls being arranged in the rotational direction. In the fourth embodiment, as shown in FIG. 30, at least parts of the one ends S2 of capillary areas 47a to 47f provided in measurement cells 40a to 40f are separated from the side walls of the measurement cells 40a to 40f, the side walls being arranged in a rotational direction. To be specific, as shown in FIG. 31A, the one end S1 on the outermost part of the capillary area 47a of the measurement cell 40a is entirely connected to one of the side walls of the measurement cell 40a in the rotational direction, and as shown in FIG. 31C, the capillary area 47a extended from the one end S1 at the outer periphery position of the capillary area 47a to the inner periphery has the one end S2 connected to, only on the innermost part, the side walls of the measurement cell 40a, the side walls being arranged in the rotational direction. As shown in FIG. 31B, the other area of the one end S2 of the capillary area 47a is separated from the side walls of the measurement cells 40a to 40f in the rotational direction. A reagent T1 is set in an area of the one end S2 of the capillary area 47a, the area being separated from the side walls of the measurement cell 40a in the rotational direction.

Figure 31D:
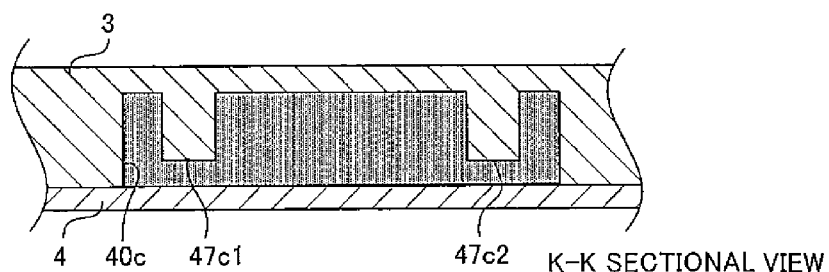
FIG. 31D is a K-K sectional view of FIG. 30.
Figure 31E:
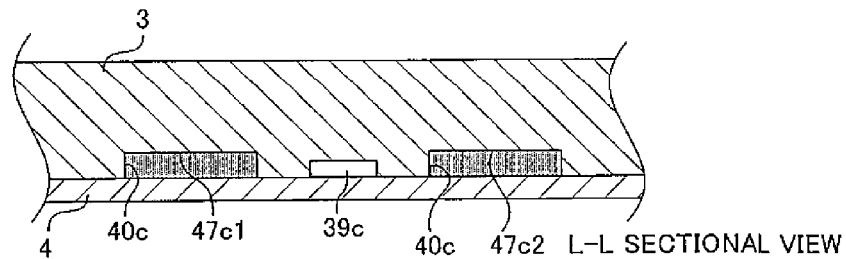
FIG. 31E is an L-L sectional view of FIG. 30.

The one end 82 of the capillary area 47a is partially connected to the side walls of the measurement cell 40a in the rotational direction, so that a capillary force for sucking a mixed solution in the capillary area 47a is larger than in the second embodiment and sufficient mixing and agitation can be expected. The same effect can be expected also in the capillary areas 40b to 40f. FIGS. 31D and 31E are K-K and L-L sectional views that show the one ends S2 of the capillary areas 47c1 and 47c2 of the measurement cell 40c.

FIGS. 30 and 31A to 31E show the case where the single reagent T1 is contained in each of the capillary areas 47a to 47f. The fourth embodiment can be similarly implemented also when reagents T1 and T2 are contained in the capillary areas 47a to 47f as in the third embodiment.

Fifth Embodiment

FIGS. 32 to 37A, 373, 37C, and 37D show a fifth embodiment of the present invention.

In the foregoing embodiments, the sample liquid dropped into the inlet 13 is drawn into the capillary cavity 19, the sample liquid is quantified through the measuring passages 39a to 39g in the analyzing device 1 in step 5, and then the quantified sample liquid is supplied to the separate measurement cells 40a to 40g by a centrifugal force. The sample liquid in the measurement cells 40a to 40f is sucked to the capillary areas 47a to 47f by a capillary force, the reagent contained in each of the capillary areas 47a to 47f is dissolved, the sample solution containing the dissolved reagent is returned to the outer peripheries of the measurement cells 40a to 40f, and then an optical measurement is conducted.

The fifth embodiment is similar to the foregoing embodiments in that a capillary area formed in a measurement cell contains a reagent, a sample liquid containing the dissolved reagent is returned to the outer periphery of the same measurement cell, and then an optical measurement is conducted. The fifth embodiment is different from the foregoing embodiments in that the sample liquid drawn into the measurement cell is quantified by the capillary area formed in the same measurement cell.

Figure 32:
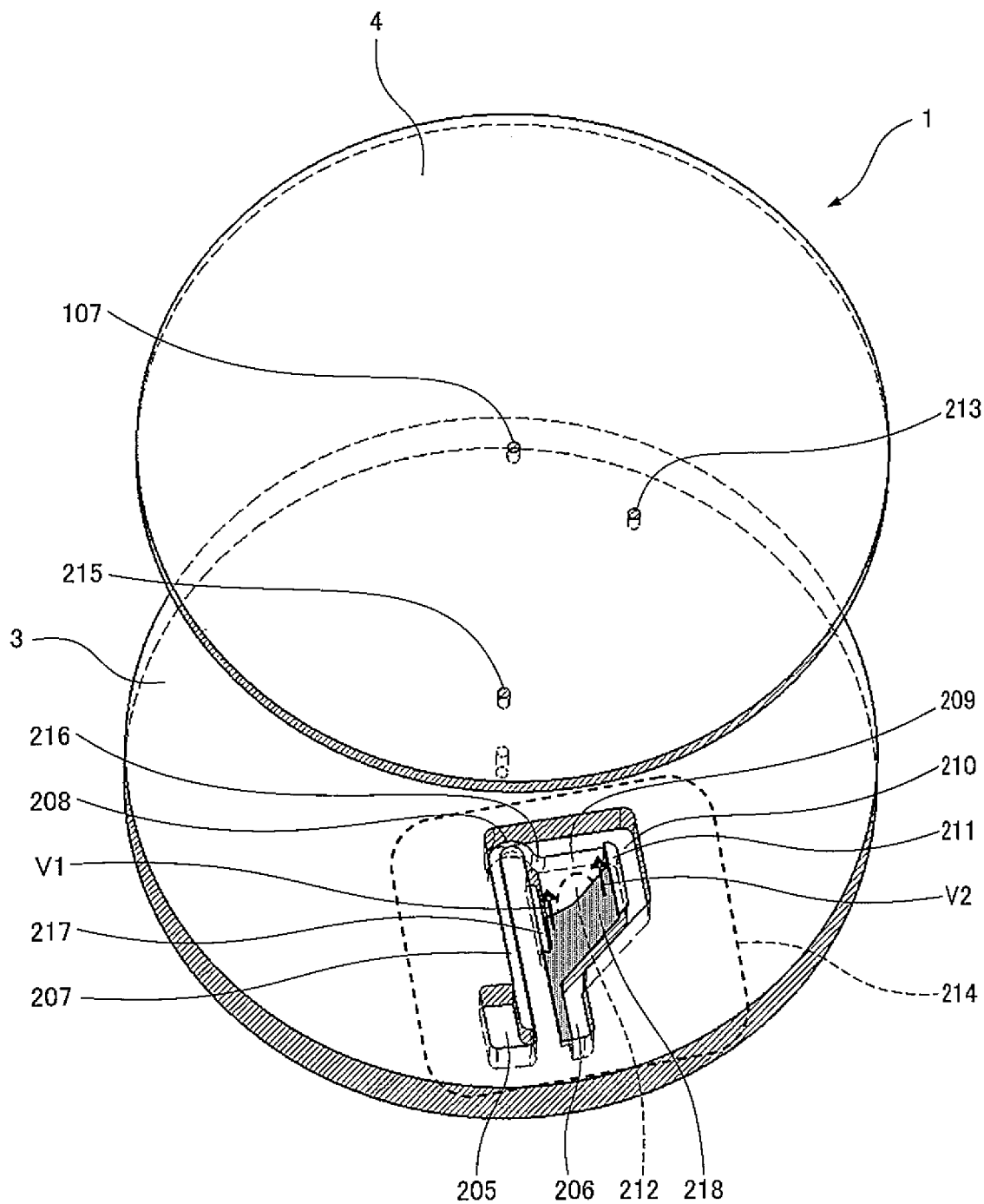
FIG. 32 is an exploded perspective view showing an analyzing device according to a fifth embodiment of the present invention.

FIG. 32 shows an analyzing device 1 according to the embodiment of the present invention.

Figure 33:
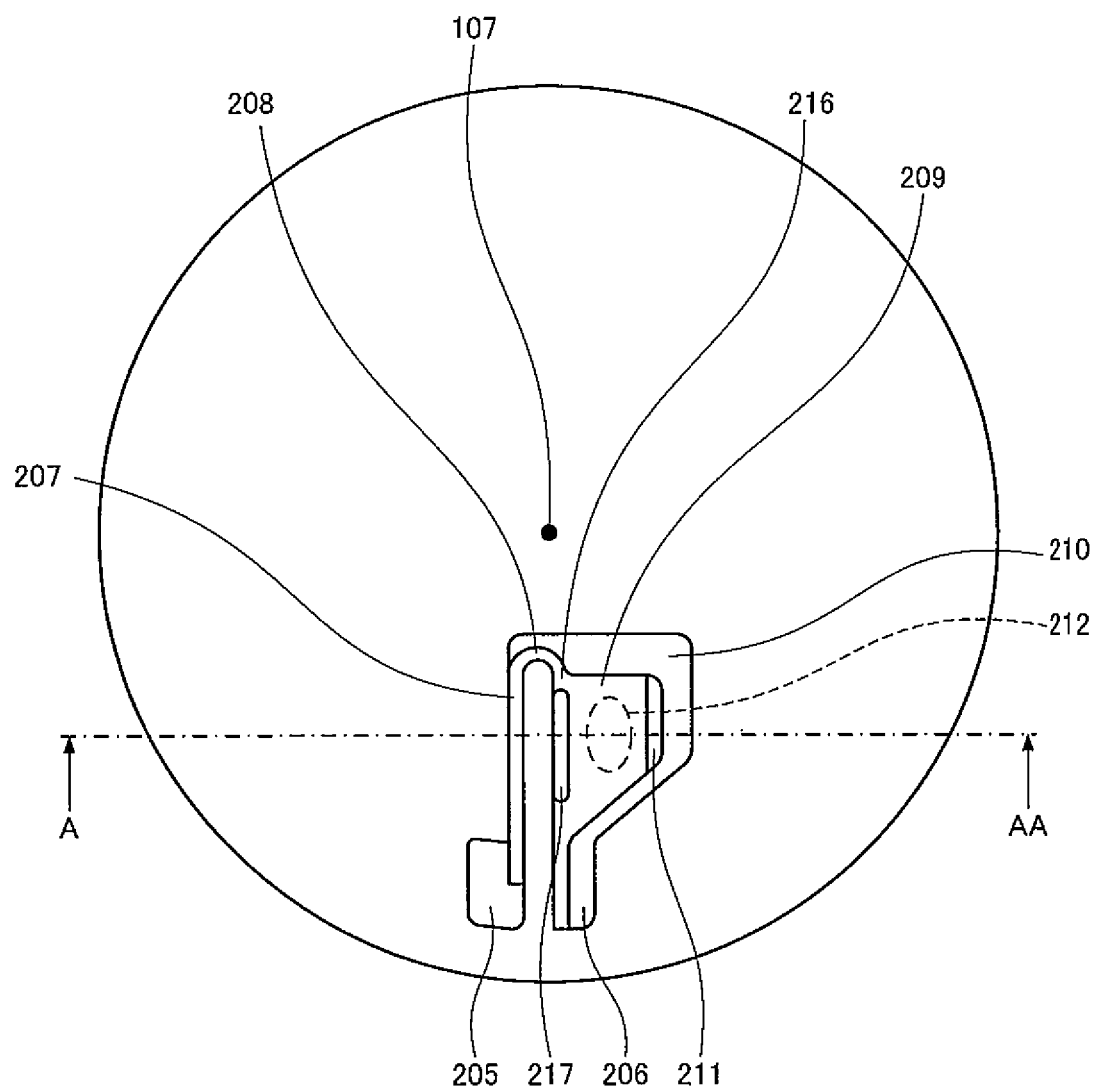
FIG. 33 is a plan view showing a surface of a base substrate 102, the surface being bonded to a cover substrate 103.
Figure 34:
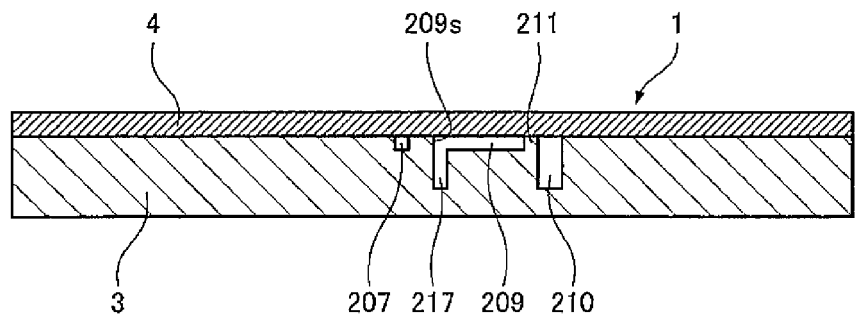
FIG. 34 is a sectional view taken along line A-AA of FIG. 33 according to the fifth embodiment.

The analyzing device 1 is configured by joining a circular base substrate 3 and a circular cover substrate 4. FIG. 33 shows a surface of the base substrate 3, the surface being bonded to the cover substrate 4. FIG. 34 is a sectional view taken along line A-AA of FIG. 33.

On the bonded surface of the base substrate 3 to the cover substrate 4, a microchannel 214 is formed that has a plurality of recessed portions with different depths and is formed of a capillary passage, a storage portion, an inspecting portion, and so on. The base substrate 3 and the cover substrate 4 are both made of a synthetic resin. The microchannel 214 is formed in the injection molding of the base substrate 3 or by cutting the base substrate 3. The cover substrate 4 is joined to the base substrate 3 so as to cover the recessed portions formed on the base substrate 3, so that the microchannel 214 is formed.

The microchannel 214 will be specifically described below.

As shown in FIG. 32, the microchannel 214 is formed from a portion around a rotation axis 107 to the outer periphery of the base substrate 3.

To be specific, the microchannel 214 is made up of a sample retaining part 205 separated from the rotation axis 107; a sample quantifying capillary 209 for the quantification of a sample liquid 218 and a reaction with a reagent 212; and a sample photometric part 206 for optically measuring the sample liquid 218 having reacted with the reagent 212. The sample photometric part 206 corresponds to the measurement cells 40a to 40f of the foregoing embodiments. The sample quantifying capillary 209 corresponds to the capillary areas 47a to 47f of the foregoing embodiments. The sample retaining part 205 and the sample quantifying capillary 209 are connected via a capillary siphon 207 having a siphon top 208 at the closest position to the rotation axis 107.

Around the sample quantifying capillary 209, a first recessed portion 210 is formed deeper than the sample quantifying capillary 209. By forming an air passage around the sample quantifying capillary 209, it is possible to prevent the entry of air bubbles during the centrifugal transfer and capillary transfer of the sample liquid 218. Although the sample quantifying capillary 209 and the capillary siphon 207 have the same depth, the sample quantifying capillary 209 may be smaller in depth than the capillary siphon 207. On the cover substrate 4, an air hole 213 is formed that allows the first recessed portion 210 to communicate with the outside.

The sample quantifying capillary 209 is formed so as to protrude in the sample retaining part 205 and the sample photometric part 206. The sample quantifying capillary 209 protruding in the sample retaining part 205 is not connected to the outer side wall of the sample retaining part 205.

The sample quantifying capillary 209 protruding in the sample photometric part 206 is connected to the outer side wall of the sample photometric part 206. With this configuration, in the sample retaining part 205, the sample liquid is transferred to the sample quantifying capillary 209 only when the liquid level of the sample liquid 218 transferred into the sample retaining part 205 reaches the sample quantifying capillary 209, thereby preventing the sample liquid 218 from excessively entering the sample quantifying capillary 209 after quantification. Further, in the sample photometric part 206, the quantified sample liquid 218 is fully transferred to the sample quantifying capillary 209 to improve reactivity between the sample liquid 218 and the reagent 212.

Further, on the sample quantifying capillary 209, a second recessed portion 217 is formed near the capillary siphon 207 and a projecting portion 211 is formed separately from the capillary siphon 207. To be specific, the second recessed portion 217 is formed along a side wall (209s) close to a connection port 216 and is in contact with the side wall (209s). As shown in FIG. 34, the second recessed portion 217 is deeper than the sample quantifying capillary 209 and the projecting portion 211 is formed in contact with the cover substrate 4.

With this configuration, the sample liquid 218 sucked by a capillary force has a flow velocity V1 on the recessed portion 211 and a flow velocity V2 on the projecting portion 211, the flow velocity V1 being lower than the flow velocity V2. Further, the sample liquid 218 can be transferred from a side separated from the capillary siphon 207, and a surface tension applied to the sample liquid 218 reduces the liquid level as the sample liquid 218 comes closer to the connection port 216. Thus it is possible to finally stop the sample liquid 218 at the connection port 216 and prevent backflow to the capillary siphon 207.

In the case where the second recessed portion 217 and the projecting portion 211 are not provided, the velocity V1 of the liquid level of the sample liquid 218 is higher than the velocity V2 in the suction of the sample liquid 218 through a capillary. Thus the sample liquid 218 enters the capillary siphon 207 before filling the sample quantifying capillary 209, so that the quantification of the sample liquid 218 cannot be maintained.

On the surface of the sample quantifying capillary 209, the reagent 212 for measuring the characteristics of the sample liquid 218 is applied. The kind of the reagent 212 may vary according to the contents of measurement.

The configuration of the analyzing device 1 will be specifically described below.

The analyzing device 1 of the present invention is made up of the base substrate 3 and the cover substrate 4 that are formed by injection molding or cutting. The base substrate 3 and the cover substrate 4 are 1 mm to 5 mm in thickness. The thicknesses of the substrates are not particularly limited as long as the microchannel 214 can be formed. The base substrate 3 and the cover substrate 4 are preferably circular in shape when the analyzing device 1 is rotated alone. In the case where the analyzing device 1 rotated on an external attachment, the shapes of the substrates are not particularly limited and thus the substrates may be varied in shape depending on a purpose. For example, a rectangle, a triangle, a sector, and other complicated shapes may be used.

The base substrate 3 and the cover substrate 4 are made of a synthetic resin in view of high moldability, high productivity, and low cost. The materials of the substrates are not particularly limited as long as the materials are bonding materials such as a glass, a silicon wafer, a metal, and a ceramic.

On the base substrate 3 and the cover substrate 4, hydrophilic treatment is performed on a part of the wall surface or over the wall surface in order to reduce a viscous drag and accelerate fluid migration in the microchannel 214 formed in each of the substrates. Hydrophilicity may be provided on a material surface by using a hydrophilic material such as a glass or adding a surface-active agent, a hydrophilic polymer, and a hydrophilizing agent, e.g., hydrophilic powder such as silica gel during molding. Methods of hydrophilic treatment include a surface treatment method using active gas of plasma, corona, ozone, fluorine, and so on and surface treatment using a surface-active agent. Hydrophilic treatment is preferably performed at least on a part of the inner walls of the sample quantifying capillary 209 and the capillary siphon 207 or over the inner walls.

In the present embodiment, the base substrate 3 and the cover substrate 4 are joined by ultrasonic welding. The base substrate 3 and the cover substrate 4 may be joined by an adhesive bonding sheet or a bonding method such as anodic bonding and laser bonding depending on a used material.

The following will specifically describe a process from the injection and transfer of the sample liquid 218 to the measurement of a component of the sample liquid 218.

Figure 36A:
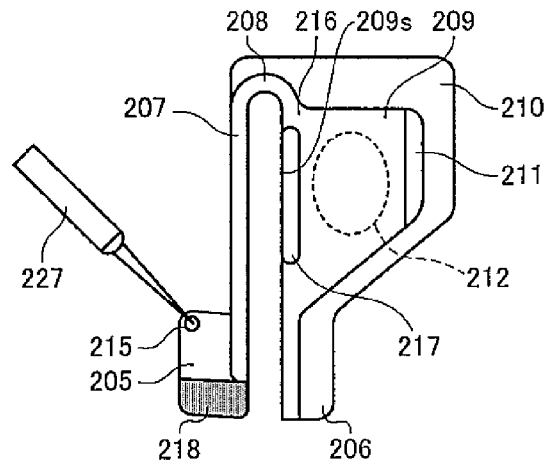
FIG. 36A is a process drawing showing a state in which a sample liquid is injected into an inlet 215 with a pipette 227.
Figure 36B:
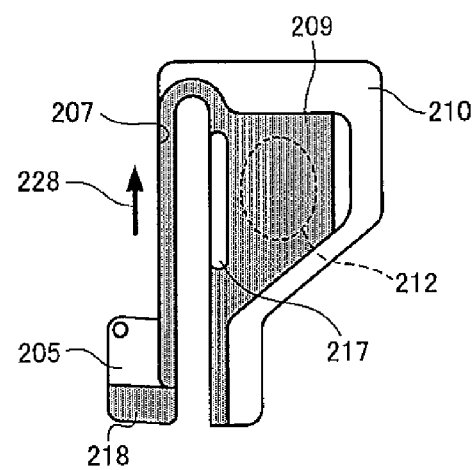
FIG. 36B is a process drawing showing a state in which the sample liquid of a sample retaining part is sucked to a sample quantifying capillary 209 through a capillary siphon.
Figure 36C:
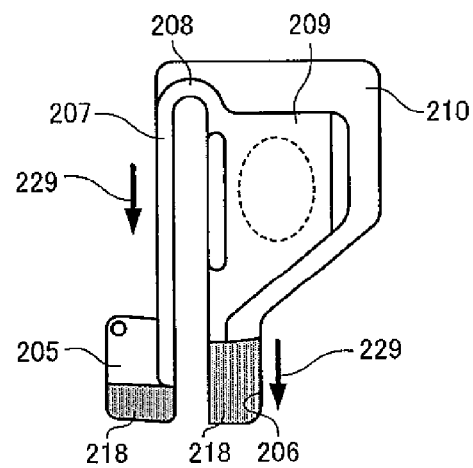
FIG. 36C is a process drawing showing a state in which the sample liquid of the sample quantifying capillary 209 is transferred to a sample retaining part 205 and a sample photometric part 206 by a centrifugal force.

FIGS. 36A, 36B, and 36C are schematic drawings for explaining a state from the injection to quantitative distribution of the sample liquid 218. FIGS. 37A to 37D are schematic drawings showing a state of the capillary transfer of the sample liquid 218.

AS shown in FIG. 36A, the sample liquid 218 is injected into the sample retaining part 205 from an inlet 215 by a pipette 227. As shown in FIG. 36B, the injected sample liquid 218 fills the sample retaining part 205, is sucked by a capillary force 228 applied in the capillary siphon 207, and is transferred to the sample quantifying capillary 209. The sample quantifying capillary 209 is filled with the sample liquid 218 after continuous injection. At this point, the sample liquid 218 is not transferred to the first and second recessed portions 210 and 217.

Since the first and second recessed portions 210 and 217 are deeper than the sample quantifying capillary 209, the capillary force 228 is interrupted at the joint of the sample quantifying capillary 209 and the first and second recessed portions 210 and 217 and the interface of the sample liquid is kept by a surface tension, thereby preventing the sample liquid from entering the first and second recessed portions 210 and 217. Further, the sample liquid 218 comes into contact with the reagent 212 applied in the sample quantifying capillary 209, so that the reagent 212 is dissolved by the sample liquid 218 and starts a reaction.

Generally, it is said that the influence of a capillary force becomes significant when a capillary has an interior diameter of 2.5 mm or less. A capillary force is the force of liquid transfer in a capillary when a liquid is moved by a force that keeps the balance of a contact angle formed by a wall surface and the liquid and a surface tension applied between gas-liquid interfaces.

Next, the analyzing device 1 is rotated about the rotation axis 107 to quantify the sample liquid 218, so that a centrifugal force 229 is generated.

As shown in FIG. 36C, the sample liquid 218 is transferred to the sample retaining part 205 and the sample photometric part 206, which are disposed on the outer periphery, by the centrifugal force 229. At this point, the sample liquid 218 is divided at the siphon top 208 and thus is quantified. Further, the sample liquid 218 containing the dissolved reagent 212 is transferred to the sample photometric part 206 and an excessive quantity of the sample liquid 218 is transferred to the sample retaining part 205.

To be specific, a rotation speed at this point is set such that a force of at least 500 G is applied to the sample liquid 218 transferred to the sample quantifying capillary 209. Thus the sample liquid 218 can be reliably transferred to the sample photometric part 206 and the sample retaining part 205. In the present embodiment, the rotation speed is set at 2500 rpm at which a centrifugal force applied to the sample liquid transferred to the sample quantifying capillary is larger than a capillary force.

Figure 37A:
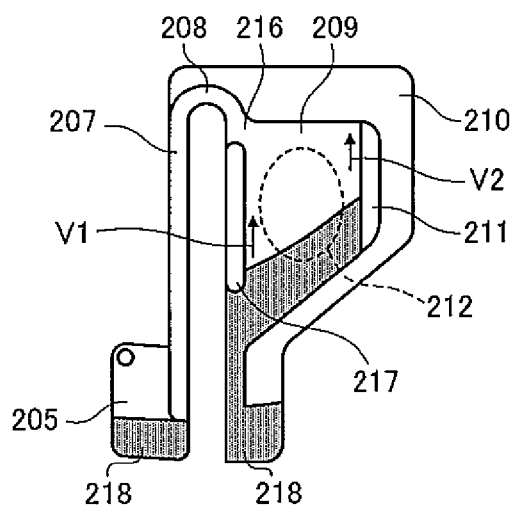
FIG. 37A is a process drawing showing a capillary transfer state of the sample liquid according to the fifth embodiment.
Figure 37B:
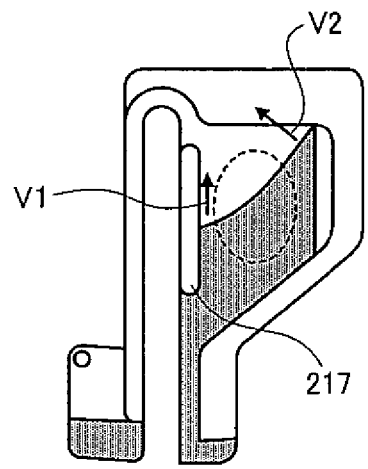
FIG. 37B is a process drawing showing a capillary transfer state of the sample liquid according to the fifth embodiment.

After the sample liquid 218 is reliably transferred to the sample retaining part 205 and the sample photometric part 206, the capillary force of the sample quantifying capillary 209 is made dominant by stopping a rotation. As shown in FIG. 37A, the sample liquid 218 quantified in the sample photometric part 206 is transferred to the sample quantifying capillary 209 again. At this point, on the side wall where the second recessed portion 217 is formed, the sample liquid 218 has a capillary force smaller than that on the side wall where the projecting portion 211 is formed. Thus between the velocity V2 of the liquid level at the projecting portion 211 and the velocity V1 of the liquid level at the second recessed portion 217, a velocity difference is made as follows:

$$V1 < V2$$

Figure 37C:
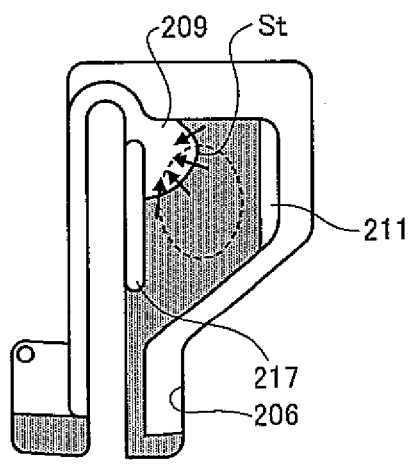
FIG. 37C is a process drawing showing a capillary transfer state of the sample liquid according to the fifth embodiment.
Figure 37D:
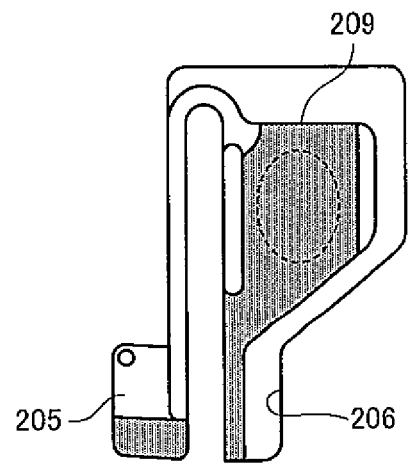
FIG. 37D is a process drawing showing a capillary transfer state of the sample liquid according to the fifth embodiment.
Figure 38A:
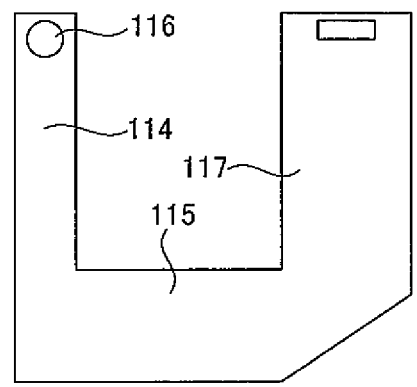
FIG. 38A is a plan view showing an analyzing device of patent document 1.
Figure 38B:
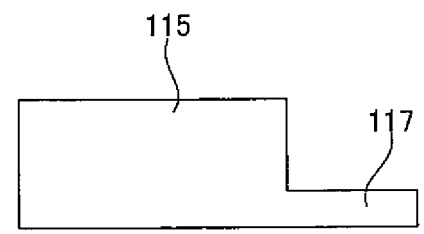
FIG. 38B is a sectional view showing the analyzing device of patent document 1.
Figure 39:
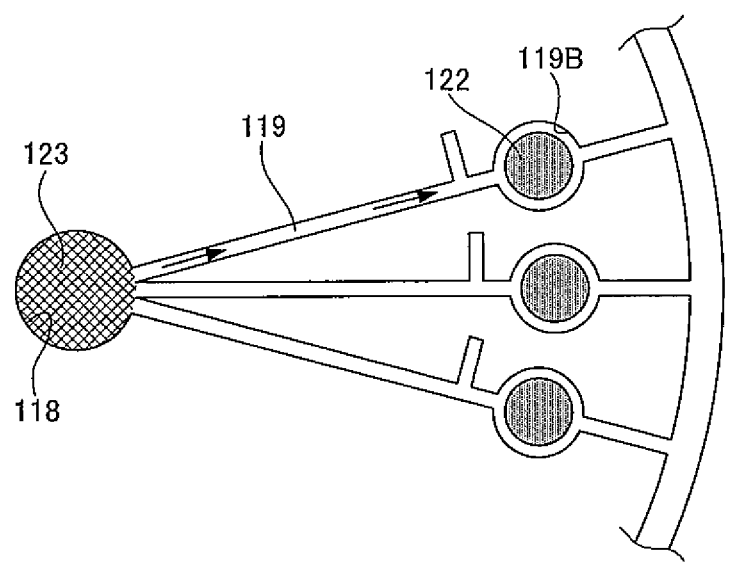
FIG. 39 is a plan view showing an analyzing device of patent document 2.

In this state, as shown in FIG. 37E, the liquid level at the velocity V2 first comes close to the connection port 216. As shown in FIG. 37C, when the liquid level at the velocity V1 and the liquid level at the velocity V2 come close to each other, a surface tension St on the liquid level of the sample liquid 218 makes dominant a force reducing the area of the liquid level, so that the liquid level is finally stopped at the connection port 216 as shown in FIG. 37D.

By using the flow mechanism of the sample liquid 218, it is possible to control the sample liquid 218 such that the liquid level reaches the connection port 216 when the sample liquid 218 is fully sucked into the sample quantifying capillary 209, and it is possible to prevent the sample liquid 218 from being transferred into the capillary siphon 207 over the siphon top 208, thereby maintaining the quantification of the sample liquid 218.

The excessive sample liquid 218 transferred to the sample retaining part 205 is retained therein because the liquid level does not reach the capillary, that is, the outer end of the rotational drive of the capillary siphon 207 is separated from the bottom of the outer periphery of the sample retaining part 205.

After the sample liquid 218 is fully transferred to the sample quantifying capillary 209, the sample liquid 218 sucked into the sample quantifying capillary 209 is transferred to the sample photometric part 206 again by a centrifugal force.

The centrifugal force generated or stopped thus transfers the sample liquid 218 between the sample photometric part 206 and the sample quantifying capillary 209 and brings the interface of the sample liquid 218 into contact with the reagent 212 several times, so that the dissolution and agitation of the reagent 212 are accelerated and the reagent 212 can be reliably dissolved.

The sample liquid 218 and the reagent 212 are mixed and agitated according to this method, and then a centrifugal force is finally generated to transfer the mixed solution to the sample photometric part 206.

The transferred mixed solution of the sample liquid 218 and the reagent 212 can be analyzed by an optical measurement method.

With the microchannel 214 in the analyzing device 1, the sample liquid 218 can be quantified and reacted with the reagent 212 in the same part.

Figure 35:
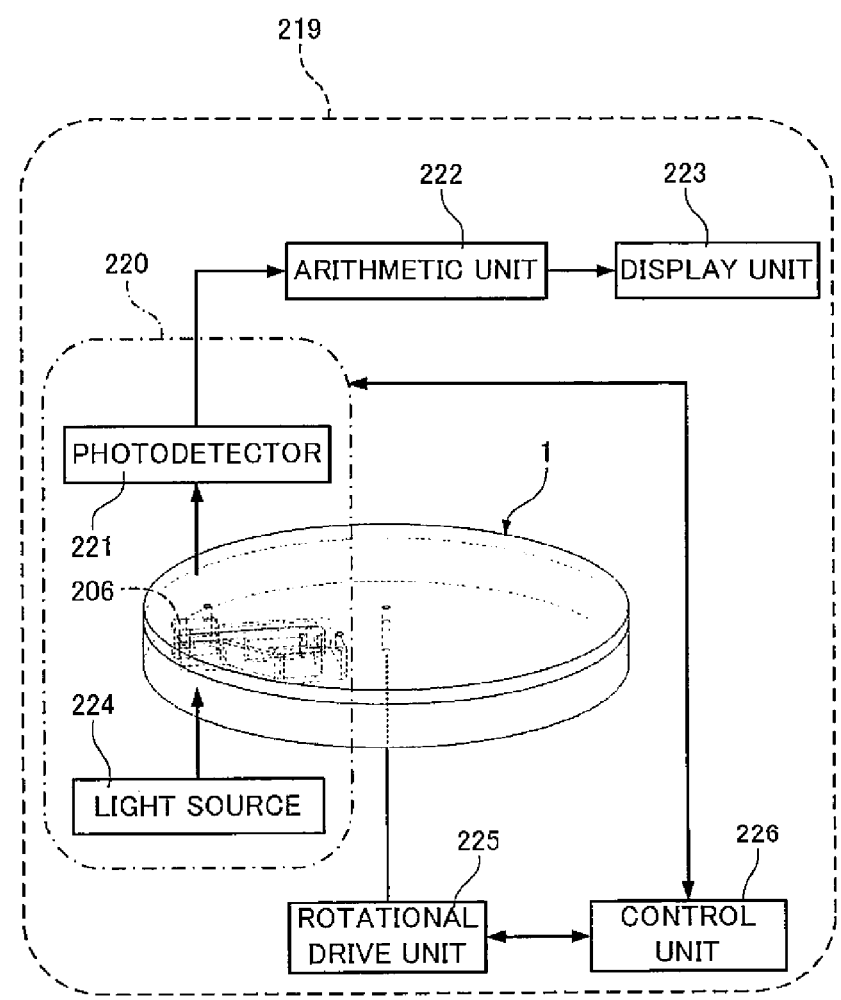
FIG. 35 is a structural diagram showing an analyzing apparatus according to the fifth embodiment.

FIG. 35 shows an analyzing apparatus 219.

The analyzing apparatus 100 is made up of a rotational drive unit 225 for rotating the analyzing device 1, an optical measurement unit 220 for optically measuring a solution in the analyzing device 1; a control unit 226 for controlling the rotation speed and direction of the analyzing device 1, the measurement timing of an optical measurement unit, and so on; an arithmetic unit 222 for calculating a measurement result by processing a signal obtained by the optical measurement unit 220; and a display unit 223 for displaying the result obtained by the arithmetic unit 222. The optical measurement unit 220 includes a light source 224 and a photodetector 221.

After the sample liquid 218 to be inspected is reacted with the reagent 212, the sample photometric part 206 is irradiated with light from the light source 224, the transmitted light is received by the photodetector 221 and is analyzed by the arithmetic unit 222, and the measurement result is displayed by the display unit 223.

During the measurement, a reaction liquid in the sample photometric part 206 fluctuates in absorbance according to the rate of the reaction. The sample photometric part 206 is irradiated with the transmitted light from the light source 224 and the quantity of transmitted light is measured by the photodetector 221. Consequently, a component of the sample liquid 218 can be analyzed by measuring a change of the quantity of light transmitted through the reaction liquid.

INDUSTRIAL APPLICABILITY

The present invention is useful as an agitator of an analyzing device used for analyzing a component of a liquid collected from an organism and the like. Since a sample liquid can be quantified and reacted with a reagent in the same part, the present invention can contribute to the proliferation of small analyzing apparatuses usable in clinics and so on.

The invention claimed is:

1. An analyzing device configured to mix a sample liquid with a reagent by rotation of the analyzing device about a rotation center to generate a centrifugal force, the analyzing device comprising:
    a measurement cell extending in a direction along which the centrifugal force is applied, the measurement cell defining a capillary area within the measurement cell, the capillary area being defined at least partially by a side wall of the measurement cell and configured to transfer the sample liquid from an outer end of the measurement cell toward the rotation center by a capillary force, the measurement cell having a plurality of side walls; and
    a microchannel structure transferring the sample liquid to the measurement cell by the centrifugal force,
    wherein the capillary area is connected to only one of the plurality of the side walls of the measurement cell.

2. The analyzing device according to claim 1, wherein the analyzing device comprises a plurality of measurement cells positioned along a circumference.

3. The analyzing device according to claim 2, wherein the measurement cells are arranged equidistant from the rotation center.

4. The analyzing device according to claim 1, wherein the capillary area contains the reagent.

5. The analyzing device according to claim 1, wherein a surface of the capillary area has a projecting portion that retains the reagent.

6. The analyzing device according to claim 1, wherein at least a part of a length of the capillary area along which the centrifugal force is applied is separated from one of the plurality of side walls of the measurement cell.

7. The analyzing device according to claim 6, wherein when the capillary area contains multiple layers of reagents, with a layer containing a reagent having a higher viscosity is placed outside of a layer containing a reagent having a lower viscosity.

8. An analyzing apparatus comprising:
    an analyzing device, the analyzing device being configured to mix a sample liquid with a reagent by rotation of the analyzing device about a rotation center to generate a centrifugal force, the analyzing device comprising:
        a measurement cell extending in a direction along which the centrifugal force is applied, the measurement cell defining a capillary area within the measurement cell, the capillary area being defined at least partially by a side wall of the measurement cell and configured to transfer the sample liquid from an outer end of the measurement cell toward the rotation center by a capillary force; and
        a microchannel structure transferring the sample liquid to the measurement cell by the
        centrifugal force; the analyzing apparatus further comprising
    a rotational drive unit for rotating the analyzing device about the rotation center;
    a control unit configured to instruct the rotational drive unit to slow or stop the rotation of the analyzing device after the sample liquid is transferred to the measurement cell, thereby allowing the sample liquid to be drawn into the capillary area by a capillary force and mixed with the reagent, and configured to instruct the rotational drive unit to accelerate the rotation after the sample liquid is mixed with the reagent, thereby causing a reaction liquid obtained by reaction of the sample liquid and the reagent to transfer from the capillary area to the outer end of the measurement cell by a centrifugal force such that the reaction liquid is agitated in the measurement cell; and
    an analyzing unit configured to access the reaction liquid and to analyze the reaction liquid.

9. An analyzing method using an analyzing device, the analyzing device being configured to mix a sample liquid with a reagent by rotation of the analyzing device about a rotation center to generate a centrifugal force, the analyzing device comprising:
    a measurement cell extending in a direction along which the centrifugal force is applied, the measurement cell defining a capillary area within the measurement cell, the capillary area being defined at least partially by a side wall of the measurement cell and configured to transfer the sample liquid from an outer end of the measurement cell toward the rotation center by a capillary force; and a microchannel structure transferring the sample liquid to the measurement cell by the centrifugal force, the analyzing method comprising:

rotating the analyzing device about the rotation center;

transferring the sample liquid to the measurement cell by the centrifugal force;

agitating the sample liquid by slowing or stopping the rotating of the analyzing device to allow the sample liquid to be drawn into the capillary area by the capillary force and mixed with the reagent, and then accelerating the rotating to cause a reaction liquid obtained by reaction of the sample liquid and the reagent to transfer from the capillary area to the outer end of the measurement cell; and accessing and analyzing the reaction liquid when the measurement cell is positioned at a reading position.

10. The analyzing method according to claim 9, wherein agitating the sample liquid comprises drawing repeatedly the sample liquid into the capillary area by the capillary force, and transferring repeatedly the reaction liquid to the outer end of the measurement cell by the centrifugal force.

11. An analyzing method using an analyzing device configured to mix a sample liquid with a reagent by rotating the analyzing device about a rotation center to generate a centrifugal force, the analyzing device comprising:

a measurement cell extending in a direction along which the centrifugal force is applied, the measurement cell defining a capillary area within the measurement cell, the capillary area being defined at least partially by a side wall of the measurement cell and configured to transfer the sample liquid from an outer end of the measurement cell toward the rotation center by a capillary force; and a microchannel structure transferring the sample liquid to the measurement cell by the centrifugal force, the analyzing method comprising:

rotating the analyzing device to supply the sample liquid to the outer end of the measurement cell by a centrifugal force and measuring the sample liquid to obtain a reference value;

drawing the sample liquid into the capillary area when a centrifugal force is smaller than a centrifugal force applied to the sample liquid during measurement of the reference value, and dissolving the reagent in the sample liquid; and applying a centrifugal force to a reaction liquid, which is obtained by reaction of the sample liquid and the reagent, to move the reaction liquid to the outer end of the measurement cell, measuring the reaction liquid to obtain a detected value, and comparing the detected value with the reference value to analyze a component of the sample liquid.

12. An analyzing apparatus comprising:

an analyzing device configured to mix a sample liquid with a reagent by rotation of the analyzing device about a rotation center to generate a centrifugal force, the analyzing device comprising:

a measurement cell extending in a direction along which the centrifugal force is applied, the measurement cell including a side wall extending in the direction along which the centrifugal force is applied, the measurement cell defining a capillary area within the measurement cell, the capillary area being defined at least partially by the side wall of the measurement cell and configured to transfer the sample liquid by a capillary force from a first end of the capillary area located at an outer end of the measurement cell toward a second end of the capillary area positioned closer to the rotation center relative to the first end, wherein at least a part of a length of the capillary area along which the centrifugal force is applied is separated from the side wall of the measurement cell; and a microchannel structure transferring the sample liquid to the measurement cell by the centrifugal force; the analyzing apparatus further comprising a rotational drive unit for rotating the analyzing device about the rotation center;

a control unit configured to instruct the rotational drive unit to slow or stop the rotation of the analyzing device after the sample liquid is transferred to the measurement cell, thereby allowing the sample liquid to be drawn into the capillary area by a capillary force and mixed with the reagent, and configured to instruct the rotational drive unit to accelerate the rotation after the sample liquid is mixed with the reagent, thereby causing a reaction liquid obtained by reaction of the sample liquid and the reagent to transfer from the capillary area to the outer end of the measurement cell by a centrifugal force such that the reaction liquid is agitated in the measurement cell; and an analyzing unit configured to access the reaction liquid and to analyze the reaction liquid.

13. An analyzing method using an analyzing device, the analyzing device being configured to mix a sample liquid with a reagent by rotation of the analyzing device about a rotation center to generate a centrifugal force, the analyzing device comprising:

a measurement cell extending in a direction along which the centrifugal force is applied, the measurement cell including a side wall extending in the direction along which the centrifugal force is applied, the measurement cell defining a capillary area within the measurement cell, the capillary area being defined at least partially by the side wall of the measurement cell and configured to transfer the sample liquid by a capillary force from a first end of the capillary area located at an outer end of the measurement cell toward a second end of the capillary area positioned closer to the rotation center relative to the first end; and a microchannel structure transferring the sample liquid to the measurement cell by the centrifugal force, wherein at least a part of a length of the capillary area along which the centrifugal force is applied is separated from the side wall of the measurement cell, the analyzing method comprising:

rotating the analyzing device;

transferring the sample liquid to the measurement cell by the centrifugal force generated by rotating;

agitating the sample liquid by slowing or stopping rotating of the analyzing device to allow the sample liquid to be drawn into the capillary area by the capillary force and mixed with the reagent, and then accelerating rotating to cause a reaction liquid obtained by reaction of the sample liquid and the reagent to transfer from the capillary area to the outer end of the measurement cell; and analyzing the reaction liquid when the measurement cell is positioned at a reading position.

* * * * *